United States Patent [19]
Lee et al.

[11] Patent Number: 5,998,134
[45] Date of Patent: Dec. 7, 1999

[54] RETINOBLASTOMA GENE-CANCER SUPPRESSOR AND REGULATOR

[75] Inventors: Wen-Hwa Lee; Eva Y-H. P. Lee, both of San Diego, Calif.

[73] Assignee: The Regents of the University of California, Oakland, Calif.

[21] Appl. No.: 08/482,627

[22] Filed: Jun. 7, 1995

Related U.S. Application Data

[63] Continuation of application No. 07/951,947, Sep. 28, 1992, which is a continuation of application No. 07/108,748, Oct. 15, 1987.

[51] Int. Cl.⁶ .................................................... C12Q 1/68
[52] U.S. Cl. ................................................................ 435/6
[58] Field of Search ................................. 435/6; 935/77, 935/78; 436/813

[56] References Cited

FOREIGN PATENT DOCUMENTS

WO 89/06703  7/1989  WIPO .

OTHER PUBLICATIONS

Angier, N., *Discover* Mar.:85–96 (1987).
Benedict et al., *Cancer Genet. and Cytogenet.* 10:311–333 (1983).
Benedict et al., *Science* 219:973–975 (1983).
Cavenee et al., *Am. J. Hum. Genet.* 36:10–24 (1984).
Cavenee et al., *Nature* 305:779–784 (1983).
Dryja et al., *Proc. Natl. Acad. Sci. USA* 83:7391–7394 (1986).
Friend et al., *Nature* 323:643–646 (1986).
Fung et al., *Science* 236:1657–1661 (1987).
Harris, Henry, *Nature* 323:582–583 (1986).
Lee et al., *Proc. Natl. Acad. Sci. USA* 83:6337–6341 (1986).
Lee et al., *Proc. Natl. Acad. Sci. USA* 83:6790–6794 (1986).
Lee et al., *Science* 235:1394–1399 (1987).
Murphree et al., *Science* 223:1028–1033 (1984).
Strong et al., *Science* 213:1501–1503 (1981).

*Primary Examiner*—Eggerton A. Campbell
*Attorney, Agent, or Firm*—Townsend and Townsend and Crew

[57] ABSTRACT

This invention relates in general to a genetic control of retinoblastoma and regulation of carcinogenicity. In particular this invention relates to the cloning, isolation, identification and sequencing of the retinoblastoma gene. The invention also relates to the method of use of the cloned retinoblastoma gene cDNA as a tool for diagnosing retinoblastoma, osteosarcoma and fibrosarcoma. Finally, the invention relates to the control and regulatory mechanisms and functions of the retinoblastoma gene in the oncogenesis.

4 Claims, 14 Drawing Sheets

```
TTCCGGTTTTTCTCAGGGGACGTTGAAATTATTTTTGTAACGGGAGTCGGGAGAGGACGGGGCGTGCCCCGCGTGCGCGCGTCGT                              87
CCTCCCCGGCGCTCCTCCACAGCTCGCTGGCTCCCGCCGCGGAAAGCGTCATGCCGCCCAAAACCCCCGAAAAACGGCCGCCACC                             174
                                         M  P  P  P  K  T  P  R  K  T   A   A   T                               (12)
GCCGCCGCTGCCGCCGCCGGGGAACCCCCGGCACCCGCCCCCCCGTAGGAGGACCAGGAGCAGGACGCGGCCGGAGGAC                                   261
 A  A  A  A  A  E   P  P  A  P  P  P  P  P  P  P   E  E  D  P  E  Q  D  S  G  P  E  D                            (41)
CTGCCCTCTCGTCAGGCTTGAGTTTGAAGAAACAGAAGAACCTGATTTTACTGCATTATGTCAGAAATTAAAGATACCAGATCATGTC                          348
 L  P  L  V  R  L  E  F  F  E  E  T  E  E  P  D  F  T  A  L  C  Q  K  L  K  I  P  D  H  V                        (70)
AGAGAGAGAGCTTGGTTAACTTGGGAGAAAGTTTCATCTGTGGATGGAGTATTGGGAGGTTATATTCAAAGAAAAAAGGAACTGTGG                           435
 R  E  R  A  W  L  T  W  E  K  V  S  S  V  D  G  V  L  G  G  Y  I  Q  K  K  K  E  L  W                           (99)
GGAATCTGTATCTTTATTGCAGCAGTTGACCTAGATGAGATGTCGTTCACTTTTACTGAGCTACAGAAAAACATAGAAATCAGTGTC                           522
 G  I  C  I  F  I  A  A  V  D  L  D  E  M  S  F  T  F  T  E  L  Q  K  M  I  E  I  S  V                           (128)
CATAAATTCTTTAACTTACTAAAGAAAATTGATACCAGTACCAAAGTTGATAATGCTATGTCAAGACTGTTGAAGAAGTATGATGTA                           609
 H  K  F  F  N  L  L  K  E  I  D  T  S  T  K  V  D  N  A  M  S  R  L  L  K  K  Y  D  V                           (157)
TTGTTTGCACTCTTCAGCAAATTGGAAAGGACATGTGAACTTATATATTGACAACCAGTTCGATATCTACTGAAATAAAT                                  696
 L  F  A  L  F  S  K  L  E  R  T  C  E  L  I  Y  L  T  Q  P  S  S  I  S  T  E  I  N                              (186)
TCTGCATTGGTGCTAAAAGTTTCTTGGATCACATTTTTATTGGCTAAAGGGGAAGTATTACAAATGGAAGATGATCTGGTCATTCA                            783
 S  A  L  V  L  K  V  S  W  I  T  F  L  L  A  K  G  E  V  L  Q  M  E  D  D  L  V  I  S                           (215)
TTTCAGTTAATGCTATGTGTCCTTGACTATTTTATTAAACTCTCCACCTCCCCATGTTGCTCAAAGAACCATATAAAACAGCTGTTATA                         870
 F  Q  L  M  L  C  V  L  D  Y  F  I  K  L  S  P  P  M  L  L  K  E  P  Y  K  T  A  V  I                           (244)
```

FIG. 7A.

```
CCCATTAATGGTTCACCTCGAACACCCAGGCGAGTCAGAACAGGAGTGCACGGATAGCAAAACAACTAGAAAATGATACAAGAATT   957
 P   I   N   G   S   P   R   T   P   R   R   G   Q   M   R   S   A   R   I   A   K   Q   L   E   N   D   T   R   I   (273)

ATTGAAGTTCTCTGTAAAGAACATGAATGTAATGATGAGGTGAAAATGTTTATTCAAAATTTTATACCTTTTATGAATTCT      1044
 I   E   V   L   C   K   E   H   E   C   M   I   D   E   V   K   M   V   Y   F   K   N   F   I   P   F   M   W   S   (302)

CTTGGACTTGTAACATCTAATGGACTTCCAGAGGTTGAAAATCTTTCTAAACGATACGAAGAAATTTATCTTAAAAATAAAGATCTA   1131
 L   G   L   V   T   S   N   G   L   P   E   V   E   N   L   S   K   R   Y   E   E   I   Y   L   K   N   K   D   L   (331)

GATGCAAGATTATTTTTGGATCATGATAAAACTCTTCAGACTGATTCTATAGACAGTTTTGAAACACAGAGAACACCCGAAAAGT   1218
 D   A   R   L   F   L   D   H   D   K   T   L   Q   T   D   S   I   D   S   F   E   T   Q   R   T   P   R   K   S   (360)

AACCTTGATGAAGAGGTGAATGTAATTCCTCCACACACTCCAGTTAGGACTGTTATGAACAACTATCCAACACTAATTAATGATGATTTTA   1305
 N   L   D   E   E   V   N   V   I   P   P   H   T   P   V   R   T   V   M   N   T   I   Q   Q   L   M   I   L   (389)

AATTCAGCAAGTGATCAACCTTCAGAAAATCTGATTTCCTATTTTAACAACTGCACAGTGAATCCAAAAGAAAGTATACTGAAAAGA   1392
 N   S   A   S   D   Q   P   S   E   N   L   I   S   Y   F   N   N   C   T   V   N   P   K   E   S   I   L   K   R   (418)

GTGAAGGATATAGGATACATCTTTAAAGAGAAATTTGCTAAAGCTGTGGGACAGGGTTGTGTCGAAATTGGATCACAGCGATACAAA   1479
 V   K   D   I   G   Y   I   F   K   E   K   F   A   K   A   V   G   Q   G   C   V   E   I   G   S   Q   R   Y   K   (447)

CTTGGAGTTCGCTTGTATTACCGAGTAATGGAATCCATGCTTAAATCAGAAGAAGAACGATTATCCATTCAAAATTTTAGCAAACTT   1566
 L   G   V   R   L   Y   Y   R   V   N   E   S   M   L   K   S   E   E   E   R   L   S   I   Q   N   F   S   K   L   (476)

CTGAATGACAACATTTTTCATATGTCTTTATTGGCGTGCGCTCTTGAGGTTGTAATGGCCACATATAGCAGAAGTACATCTCAGAAT   1653
 L   N   D   N   I   F   H   M   S   L   L   A   C   A   L   E   V   V   M   A   T   Y   S   R   S   T   S   Q   N   (505)

CTTGATTCTGGAACAGATTGTCTTTCCCATGGATTCTGAATGTGCTTAATTTAAAAGCCCTTTGATTTTTACAAAGTGATCGAAAGT    1740
 L   D   S   G   T   D   L   S   F   P   W   I   L   N   V   L   N   L   K   A   F   D   F   Y   K   V   I   E   S   (534)
```

*FIG. 7B.*

```
TTTATCAAAGCAGAAGGCAACTTGACAACTTGAACAACTTAGAACGATGTGAACATCATGAATCCCTTGCATGG  1827
 F  I  K  A  E  G  N  L  T  R  E  M  I  K  N  L  E  R  C  E  N  R  I  M  E  S  L  A  W   (563)

CTCTCAGATTCACCTTTATTTGATCTTATTAAACAATCAAAGGACCGAGAAGGACCAACTGATCACTTGTCCTCTT  1914
 L  S  D  S  P  L  F  D  L  I  K  Q  S  K  D  R  E  G  P  T  D  H  L  E  S  A  C  P  L   (592)

AATCTTCCTCTCCAGAATAATCACACTGCAGCAGATATGTATCTTTCCTGTAAGATCTCCAAAGAAAAAGGTTCAACTACGCGT  2001
 N  L  P  L  Q  N  N  H  T  A  A  D  M  Y  L  S  P  V  R  S  P  K  K  K  G  S  T  T  R   (621)

GTAAATTCTACTGCAAATGCAGAGACACAAGCAACCTCAGCCTTCCAGACCCAGAAGCCATTGAAATCTACCTCTCTTTCACTGTTT  2088
 V  N  S  T  A  N  A  E  T  Q  A  T  S  A  F  Q  T  Q  K  P  L  K  S  T  S  L  S  L  F   (650)

TATAAAAAGTGTATCGGCTAGCCTATCTCCGGCTAAATACACTTTGTGAACGCCCTTCTGTCTGAGCACCCAGAATTAGAACATATC  2175
 Y  K  K  V  Y  R  L  A  Y  L  R  L  N  T  L  C  E  R  L  L  S  E  N  P  E  L  E  H  I   (679)

ATCTGGACCCCTTTTCCAGCACACCCTGCAGAATGAGTAGTTGGACCAAATTATGATGTGTTCCATG  2262
 I  W  T  L  F  Q  N  T  L  Q  N  E  Y  E  L  N  R  D  R  N  L  D  Q  I  N  N  C  S  N   (708)

TATGGCATATGCAAAGTGAAGAATATAGACCTTAAATTCAAAATCATTGTAACAGCATACAAGGATCTTCCTCATGCTGTTCAGGAG  2349
 Y  G  I  C  K  V  K  N  I  D  L  K  F  K  I  I  V  T  A  Y  K  D  L  P  H  A  V  Q  E   (737)

ACATTCAAACGTGTTTTGATCAAAGAAGAGGAGTATGATTCTATTATAGTATTCTATAACTCGGTCTTCAATGCAGAGACTGAAAACA  2436
 T  F  K  R  V  L  I  K  E  E  Y  D  S  I  I  V  F  Y  N  S  V  F  N  Q  R  L  K  T   (766)

AATATTTTGCAGTATGCTTCCACCAGGCCCCCTACCTTGTCACCAATACCTCACATTCCTCGAAGCCCTTACAAGTTTCCTAGTTCA  2523
 N  I  L  Q  Y  A  S  T  R  P  P  T  L  S  P  I  P  H  I  P  R  S  P  Y  K  F  P  S  S   (795)

CCCTTACGGATTCCTGGAGGGAACATCTATATTTCACCCCTGAAGAGTCCATATAAAATTCAGAAGGTCTGCCAACACCAACAAAA  2610
 P  L  R  I  P  G  G  N  I  Y  I  S  P  L  K  S  P  Y  K  I  S  E  G  L  P  T  P  T  K   (824)
```

FIG. 7C.

```
ATGACTCCAAGATCAAGAATCTTAGTATCAATTGGTGAATCATTCGGGACTTCTGAGAAGTTCCAGAAAATAAATCAGATGGTATGT  2697
 N  T  P  R  S  R  I  L  V  S  I  G  E  S  F  G  T  S  E  K  F  Q  K  I  N  Q  M  V  C   (853)

AACAGGCGACCGTGTGCTCAAAAGAATGCTGAAGGAACAACCCCTCCTAAACCACTGAAAAAACTACGCTTTGATATTGAAGGATCA  2784
 N  S  D  R  V  L  K  R  S  A  E  G  S  N  P  P  K  P  L  K  K  L  R  F  D  I  E  G  S   (882)

GATGAAGCAGATGGAAGTAAACATCTCCCAGGAGAGTCCAAATTTCAGCAGAAACTGGCAGAAAATGACTTCTACTCGAACACGAATG  2871
 D  E  A  D  G  S  K  N  L  P  G  E  S  K  F  Q  Q  K  L  A  E  N  T  S  T  R  T  R  N   (911)

CAAAAGCAGAAAATGAATGATAGCATGGATACCTCAAACAAGGAAGAGAAATGAGGATCTCAGGACCTTGGTGGACACTGTGTACAC  2958
 Q  K  Q  K  M  N  D  S  M  D  T  S  N  K  E  E  K                                         (928)

CTCTGGATTCATTGTCTCTCACAGATGTGACTGTAT..................................................TO 4757
```

FIG. 7D.

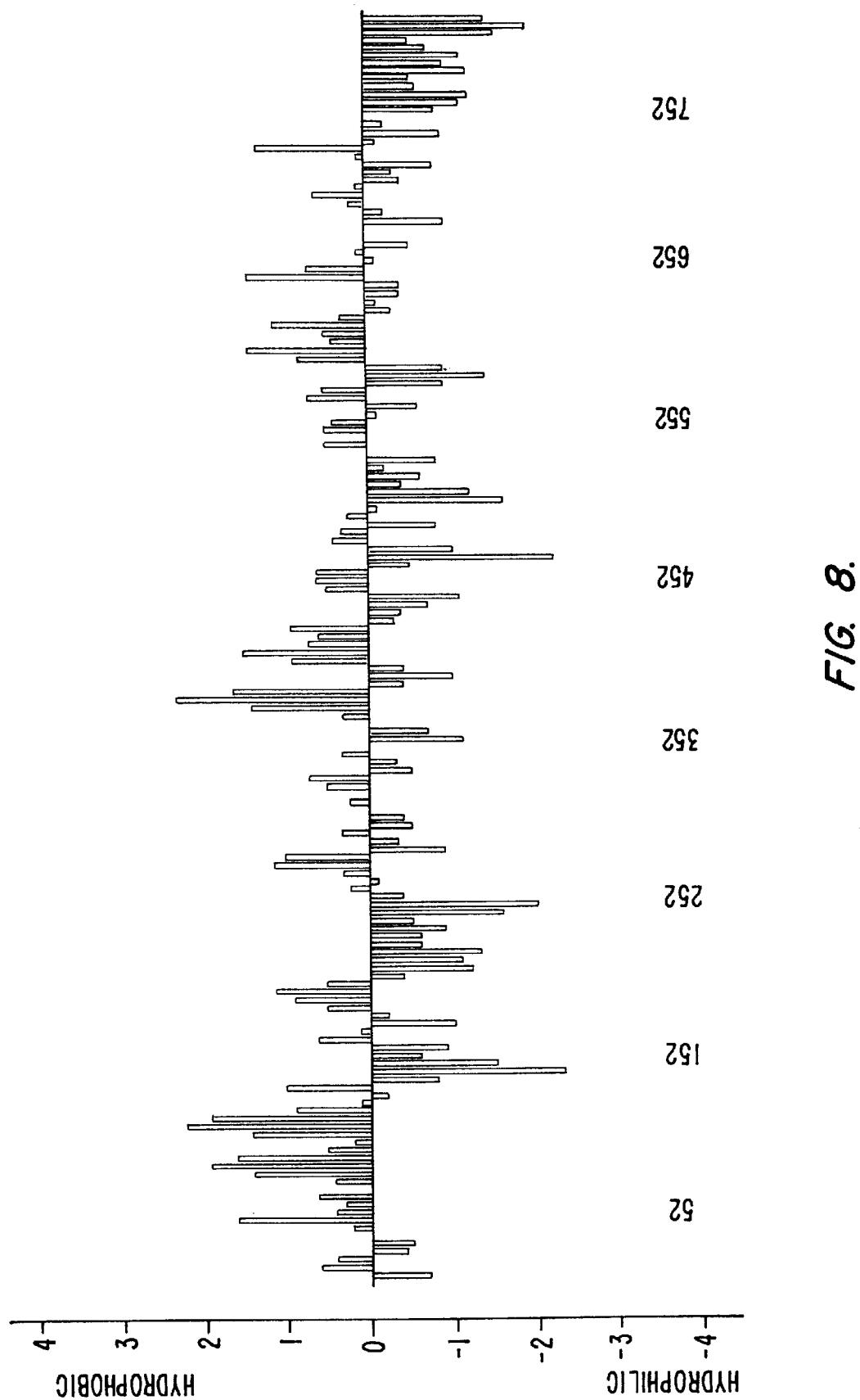

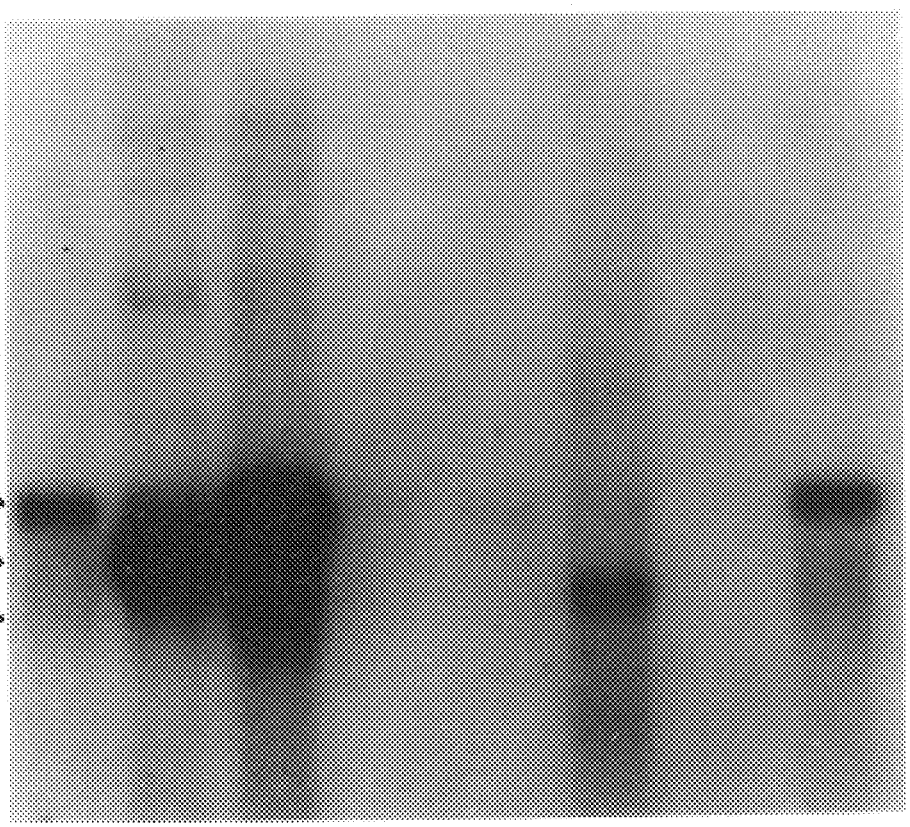
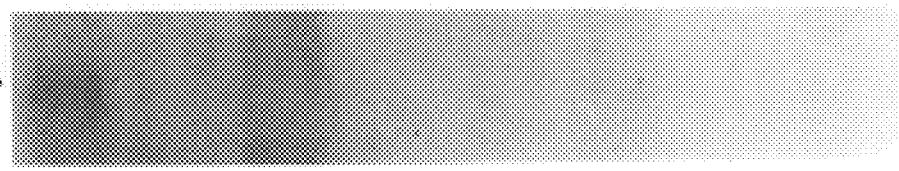
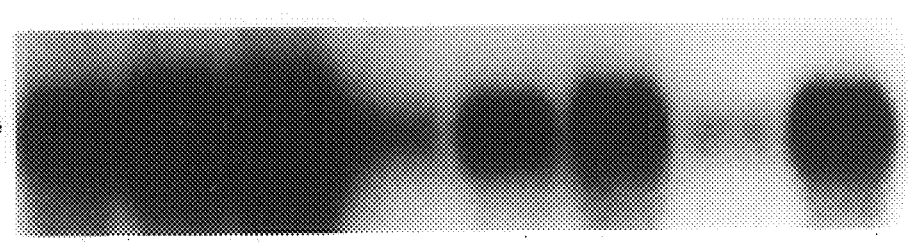
FIG. 9.

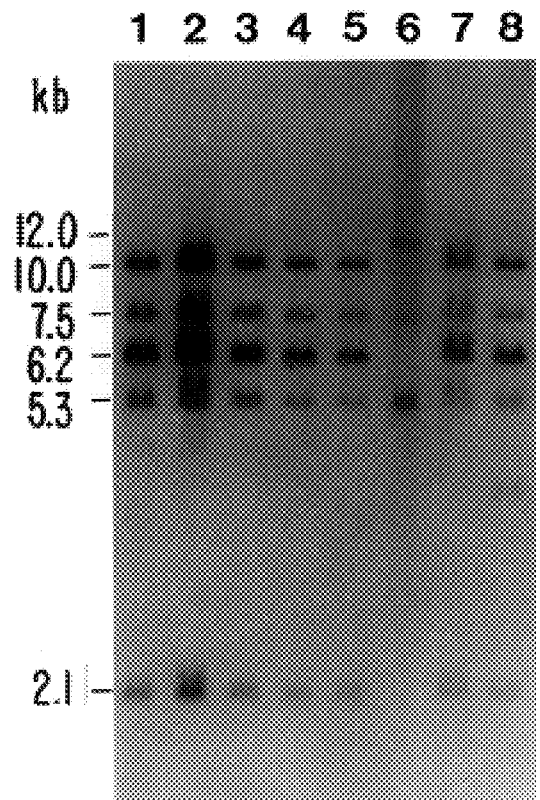
FIG. IIA.
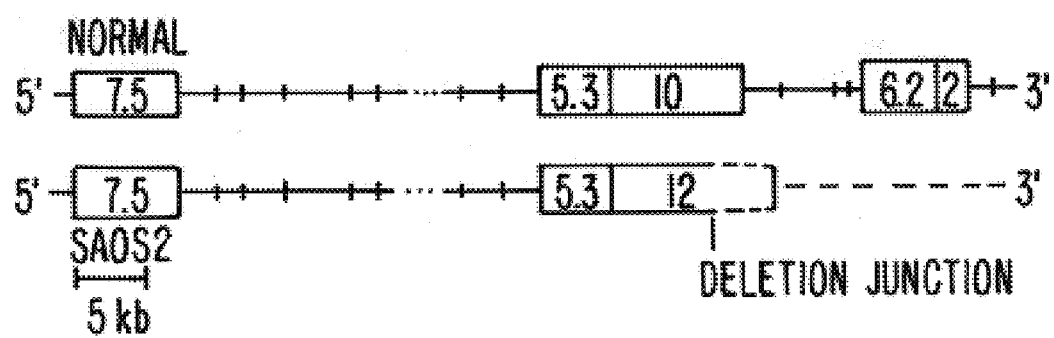
FIG. IIB.

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
           (A) LENGTH: 23 base pairs
           (B) TYPE: nucleic acid
           (C) STRANDEDNESS: single
           (D) TOPOLOGY: linear (xi) SEQUENCE DESCRIPTION: SEQ ID NO:1:

CCNGGRTTYT TNAGNGCDCA RAT                                              23

(2) INFORMATION FOR SEQ ID NO:2:

(i) SEQUENCE CHARACTERISTICS:
           (A) LENGTH: 8 amino acids
           (B) TYPE: amino acid
           (C) STRANDEDNESS:
           (D) TOPOLOGY: linear (xi) SEQUENCE DESCRIPTION: SEQ ID NO:2:

Ile Lys Ala Leu Lys Asn Pro Gly
1               5

(2) INFORMATION FOR SEQ ID NO:3:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:3:

ATYTGYGCNAARAAYCCNGG                                                   20

(2) INFORMATION FOR SEQ ID NO:4:

(i) SEQUENCE CHARACTERISTICS:
           (A) LENGTH: 2994 base pairs
           (B) TYPE: nucleic acid
           (C) STRANDEDNESS: single
           (D) TOPOLOGY: linear (ix) FEATURE:
           (A) NAME/KEY: CDS
           (B) LOCATION: 139..2924

(xi) SEQUENCE DESCRIPTION: SEQ ID NO:4:

TTCCGGTTTT TCTCAGGGGA CGTTGAAATT ATTTTTGTAA CGGGAGTCGG GAGAGGACGG       60

GGCGTGCCCC GCGTGCGCGC GCGTCGTCCT CCCCGGCGCT CCTCCACAGC TCGCTGGCTC      120

CCGCCGCGGA AAGGCGTC ATG CCG CCC AAA ACC CCC CGA AAA ACG GCC GCC       171
                    Met Pro Pro Lys Thr Pro Arg Lys Thr Ala Ala
                     1               5                  10

ACC GCC GCC GCT GCC GCC GCG GAA CCC CCG GCA CCG CCG CCG CCC           219
Thr Ala Ala Ala Ala Ala Ala Glu Pro Pro Ala Pro Pro Pro Pro
                 15                  20                  25

CCT CCG GAG GAG GAC CCA GAG CAG GAC AGC GGC CCG GAG GAC CTG CCT       267
Pro Pro Glu Glu Asp Pro Glu Gln Asp Ser Gly Pro Glu Asp Leu Pro
         30                  35                  40

```
CTC GTC AGG CTT GAG TTT GAA GAA ACA GAA GAA CCT GAT TTT ACT GCA        315
Leu Val Arg Leu Glu Phe Glu Glu Thr Glu Glu Pro Asp Phe Thr Ala
 45                  50                  55

TTA TGT CAG AAA TTA AAG ATA CCA GAT CAT GTC AGA GAG AGA GCT TGG        363
Leu Cys Gln Lys Leu Lys Ile Pro Asp His Val Arg Glu Arg Ala Trp
 60                  65                  70                  75

TTA ACT TGG GAG AAA GTT TCA TCT GTG GAT GGA GTA TTG GGA GGT TAT        411
Leu Thr Trp Glu Lys Val Ser Ser Val Asp Gly Val Leu Gly Gly Tyr
                 80                  85                  90

ATT CAA AAG AAA AAG GAA CTG TGG GGA ATC TGT ATC TTT ATT GCA GCA        459
Ile Gln Lys Lys Lys Glu Leu Trp Gly Ile Cys Ile Phe Ile Ala Ala
                 95                 100                 105

GTT GAC CTA GAT GAG ATG TCG TTC ACT TTT ACT GAG CTA CAG AAA AAC        507
Val Asp Leu Asp Glu Met Ser Phe Thr Phe Thr Glu Leu Gln Lys Asn
            110                 115                 120

ATA GAA ATC AGT GTC CAT AAA TTC TTT AAC TTA CTA AAA GAA ATT GAT        555
Ile Glu Ile Ser Val His Lys Phe Phe Asn Leu Leu Lys Glu Ile Asp
125                 130                 135

ACC AGT ACC AAA GTT GAT AAT GCT ATG TCA AGA CTG TTG AAG AAG TAT        603
Thr Ser Thr Lys Val Asp Asn Ala Met Ser Arg Leu Leu Lys Lys Tyr
140                 145                 150                 155

GAT GTA TTG TTT GCA CTC TTC AGC AAA TTG GAA AGG ACA TGT GAA CTT        651
Asp Val Leu Phe Ala Leu Phe Ser Lys Leu Glu Arg Thr Cys Glu Leu
                160                 165                 170

ATA TAT TTG ACA CAA CCC AGC AGT TCG ATA TCT ACT GAA ATA AAT TCT        699
Ile Tyr Leu Thr Gln Pro Ser Ser Ser Ile Ser Thr Glu Ile Asn Ser
                175                 180                 185

GCA TTG GTG CTA AAA GTT TCT TGG ATC ACA TTT TTA TTA GCT AAA GGG        747
Ala Leu Val Leu Lys Val Ser Trp Ile Thr Phe Leu Leu Ala Lys Gly
                190                 195                 200

GAA GTA TTA CAA ATG GAA GAT GAT CTG GTG ATT TCA TTT CAG TTA ATG        795
Glu Val Leu Gln Met Glu Asp Asp Leu Val Ile Ser Phe Gln Leu Met
205                 210                 215

CTA TGT GTC CTT GAC TAT TTT ATT AAA CTC TCA CCT CCC ATG TTG CTC        843
Leu Cys Val Leu Asp Tyr Phe Ile Lys Leu Ser Pro Pro Met Leu Leu
220                 225                 230                 235

AAA GAA CCA TAT AAA ACA GCT GTT ATA CCC ATT AAT GGT TCA CCT CGA        891
Lys Glu Pro Tyr Lys Thr Ala Val Ile Pro Ile Asn Gly Ser Pro Arg
                240                 245                 250

ACA CCC AGG CGA GGT CAG AAC AGG AGT GCA CGG ATA GCA AAA CAA CTA        939
Thr Pro Arg Arg Gly Gln Asn Arg Ser Ala Arg Ile Ala Lys Gln Leu
                255                 260                 265

GAA AAT GAT ACA AGA ATT ATT GAA GTT CTC TGT AAA GAA CAT GAA TGT        987
Glu Asn Asp Thr Arg Ile Ile Glu Val Leu Cys Lys Glu His Glu Cys
                270                 275                 280

AAT ATA GAT GAG GTG AAA AAT GTT TAT TTC AAA AAT TTT ATA CCT TTT       1035
Asn Ile Asp Glu Val Lys Asn Val Tyr Phe Lys Asn Phe Ile Pro Phe
285                 290                 295

ATG AAT TCT CTT GGA CTT GTA ACA TCT AAT GGA CTT CCA GAG GTT GAA       1083
Met Asn Ser Leu Gly Leu Val Thr Ser Asn Gly Leu Pro Glu Val Glu
300                 305                 310                 315

AAT CTT TCT AAA CGA TAC GAA GAA ATT TAT CTT AAA AAT AAA GAT CTA       1131
Asn Leu Ser Lys Arg Tyr Glu Glu Ile Tyr Leu Lys Asn Lys Asp Leu
                320                 325                 330

GAT GCA AGA TTA TTT TTG GAT CAT GAT AAA ACT CTT CAG ACT GAT TCT       1179
Asp Ala Arg Leu Phe Leu Asp His Asp Lys Thr Leu Gln Thr Asp Ser
                335                 340                 345

ATA GAC AGT TTT GAA ACA CAG AGA ACA CCA CGA AAA AGT AAC CTT GAT       1227
Ile Asp Ser Phe Glu Thr Gln Arg Thr Pro Arg Lys Ser Asn Leu Asp
350                 355                 360
```

```
GAA GAG GTG AAT GTA ATT CCT CCA CAC ACT CCA GTT AGG ACT GTT ATG        1275
Glu Glu Val Asn Val Ile Pro Pro His Thr Pro Val Arg Thr Val Met
365                 370                 375

AAC ACT ATC CAA CAA TTA ATG ATG ATT TTA AAT TCA GCA AGT GAT CAA        1323
Asn Thr Ile Gln Gln Leu Met Met Ile Leu Asn Ser Ala Ser Asp Gln
380                 385                 390                 395

CCT TCA GAA AAT CTG ATT TCC TAT TTT AAC AAC TGC ACA GTG AAT CCA        1371
Pro Ser Glu Asn Leu Ile Ser Tyr Phe Asn Asn Cys Thr Val Asn Pro
                400                 405                 410

AAA GAA AGT ATA CTG AAA AGA GTG AAG GAT ATA GGA TAC ATC TTT AAA        1419
Lys Glu Ser Ile Leu Lys Arg Val Lys Asp Ile Gly Tyr Ile Phe Lys
            415                 420                 425

GAG AAA TTT GCT AAA GCT GTG GGA CAG GGT TGT GTC GAA ATT GGA TCA        1467
Glu Lys Phe Ala Lys Ala Val Gly Gln Gly Cys Val Glu Ile Gly Ser
        430                 435                 440

CAG CGA TAC AAA CTT GGA GTT CGC TTG TAT TAC CGA GTA ATG GAA TCC        1515
Gln Arg Tyr Lys Leu Gly Val Arg Leu Tyr Tyr Arg Val Met Glu Ser
    445                 450                 455

ATG CTT AAA TCA GAA GAA GAA CGA TTA TCC ATT CAA AAT TTT AGC AAA        1563
Met Leu Lys Ser Glu Glu Glu Arg Leu Ser Ile Gln Asn Phe Ser Lys
460                 465                 470                 475

CTT CTG AAT GAC AAC ATT TTT CAT ATG TCT TTA TTG GCG TGC GCT CTT        1611
Leu Leu Asn Asp Asn Ile Phe His Met Ser Leu Leu Ala Cys Ala Leu
                480                 485                 490

GAG GTT GTA ATG GCC ACA TAT AGC AGA AGT ACA TCT CAG AAT CTT GAT        1659
Glu Val Val Met Ala Thr Tyr Ser Arg Ser Thr Ser Gln Asn Leu Asp
            495                 500                 505

TCT GGA ACA GAT TTG TCT TTC CCA TGG ATT CTG AAT GTG CTT AAT TTA        1707
Ser Gly Thr Asp Leu Ser Phe Pro Trp Ile Leu Asn Val Leu Asn Leu
        510                 515                 520

AAA GCC TTT GAT TTT TAC AAA GTG ATC GAA AGT TTT ATC AAA GCA GAA        1755
Lys Ala Phe Asp Phe Tyr Lys Val Ile Glu Ser Phe Ile Lys Ala Glu
    525                 530                 535

GGC AAC TTG ACA AGA GAA ATG ATA AAA CAT TTA GAA CGA TGT GAA CAT        1803
Gly Asn Leu Thr Arg Glu Met Ile Lys His Leu Glu Arg Cys Glu His
540                 545                 550                 555

CGA ATC ATG GAA TCC CTT GCA TGG CTC TCA GAT TCA CCT TTA TTT GAT        1851
Arg Ile Met Glu Ser Leu Ala Trp Leu Ser Asp Ser Pro Leu Phe Asp
                560                 565                 570

CTT ATT AAA CAA TCA AAG GAC CGA GAA GGA CCA ACT GAT CAC CTT GAA        1899
Leu Ile Lys Gln Ser Lys Asp Arg Glu Gly Pro Thr Asp His Leu Glu
            575                 580                 585

TCT GCT TGT CCT CTT AAT CTT CCT CTC CAG AAT AAT CAC ACT GCA GCA        1947
Ser Ala Cys Pro Leu Asn Leu Pro Leu Gln Asn Asn His Thr Ala Ala
        590                 595                 600

GAT ATG TAT CTT TCT CCT GTA AGA TCT CCA AAG AAA AAA GGT TCA ACT        1995
Asp Met Tyr Leu Ser Pro Val Arg Ser Pro Lys Lys Lys Gly Ser Thr
    605                 610                 615

ACG CGT GTA AAT TCT ACT GCA AAT GCA GAG ACA CAA GCA ACC TCA GCC        2043
Thr Arg Val Asn Ser Thr Ala Asn Ala Glu Thr Gln Ala Thr Ser Ala
620                 625                 630                 635

TTC CAG ACC CAG AAG CCA TTG AAA TCT ACC TCT CTT TCA CTG TTT TAT        2091
Phe Gln Thr Gln Lys Pro Leu Lys Ser Thr Ser Leu Ser Leu Phe Tyr
                640                 645                 650

AAA AAA GTG TAT CGG CTA GCC TAT CTC CGG CTA AAT ACA CTT TGT GAA        2139
Lys Lys Val Tyr Arg Leu Ala Tyr Leu Arg Leu Asn Thr Leu Cys Glu
            655                 660                 665

CGC CTT CTG TCT GAG CAC CCA GAA TTA GAA CAT ATC ATC TGG ACC CTT        2187
Arg Leu Leu Ser Glu His Pro Glu Leu Glu His Ile Ile Trp Thr Leu
        670                 675                 680
```

-continued

| | | |
|---|---|---|
| TTC CAG CAC ACC CTG CAG AAT GAG TAT GAA CTC ATG AGA GAC AGG CAT<br>Phe Gln His Thr Leu Gln Asn Glu Tyr Glu Leu Met Arg Asp Arg His<br>685                      690                      695 | | 2235 |
| TTG GAC CAA ATT ATG ATG TGT TCC ATG TAT GGC ATA TGC AAA GTG AAG<br>Leu Asp Gln Ile Met Met Cys Ser Met Tyr Gly Ile Cys Lys Val Lys<br>700                705                  710                  715 | | 2283 |
| AAT ATA GAC CTT AAA TTC AAA ATC ATT GTA ACA GCA TAC AAG GAT CTT<br>Asn Ile Asp Leu Lys Phe Lys Ile Ile Val Thr Ala Tyr Lys Asp Leu<br>                      720                      725                  730 | | 2331 |
| CCT CAT GCT GTT CAG GAG ACA TTC AAA CGT GTT TTG ATC AAA GAA GAG<br>Pro His Ala Val Gln Glu Thr Phe Lys Arg Val Leu Ile Lys Glu Glu<br>                735                      740                  745 | | 2379 |
| GAG TAT GAT TCT ATT ATA GTA TTC TAT AAC TCG GTC TTC ATG CAG AGA<br>Glu Tyr Asp Ser Ile Ile Val Phe Tyr Asn Ser Val Phe Met Gln Arg<br>750                      755                  760 | | 2427 |
| CTG AAA ACA AAT ATT TTG CAG TAT GCT TCC ACC AGG CCC CCT ACC TTG<br>Leu Lys Thr Asn Ile Leu Gln Tyr Ala Ser Thr Arg Pro Pro Thr Leu<br>765                      770                  775 | | 2475 |
| TCA CCA ATA CCT CAC ATT CCT CGA AGC CCT TAC AAG TTT CCT AGT TCA<br>Ser Pro Ile Pro His Ile Pro Arg Ser Pro Tyr Lys Phe Pro Ser Ser<br>780                      785                  790                  795 | | 2523 |
| CCC TTA CGG ATT CCT GGA GGG AAC ATC TAT ATT TCA CCC CTG AAG AGT<br>Pro Leu Arg Ile Pro Gly Gly Asn Ile Tyr Ile Ser Pro Leu Lys Ser<br>                800                      805                  810 | | 2571 |
| CCA TAT AAA ATT TCA GAA GGT CTG CCA ACA CCA ACA AAA ATG ACT CCA<br>Pro Tyr Lys Ile Ser Glu Gly Leu Pro Thr Pro Thr Lys Met Thr Pro<br>                815                      820                  825 | | 2619 |
| AGA TCA AGA ATC TTA GTA TCA ATT GGT GAA TCA TTC GGG ACT TCT GAG<br>Arg Ser Arg Ile Leu Val Ser Ile Gly Glu Ser Phe Gly Thr Ser Glu<br>830                      835                  840 | | 2667 |
| AAG TTC CAG AAA ATA AAT CAG ATG GTA TGT AAC AGC GAC CGT GTG CTC<br>Lys Phe Gln Lys Ile Asn Gln Met Val Cys Asn Ser Asp Arg Val Leu<br>845                      850                  855 | | 2715 |
| AAA AGA AGT GCT GAA GGA AGC AAC CCT CCT AAA CCA CTG AAA AAA CTA<br>Lys Arg Ser Ala Glu Gly Ser Asn Pro Pro Lys Pro Leu Lys Lys Leu<br>860                      865                  870                  875 | | 2763 |
| CGC TTT GAT ATT GAA GGA TCA GAT GAA GCA GAT GGA AGT AAA CAT CTC<br>Arg Phe Asp Ile Glu Gly Ser Asp Glu Ala Asp Gly Ser Lys His Leu<br>                880                      885                  890 | | 2811 |
| CCA GGA GAG TCC AAA TTT CAG CAG AAA CTG GCA GAA ATG ACT TCT ACT<br>Pro Gly Glu Ser Lys Phe Gln Gln Lys Leu Ala Glu Met Thr Ser Thr<br>                895                      900                  905 | | 2859 |
| CGA ACA CGA ATG CAA AAG CAG AAA ATG AAT GAT AGC ATG GAT ACC TCA<br>Arg Thr Arg Met Gln Lys Gln Lys Met Asn Asp Ser Met Asp Thr Ser<br>910                      915                  920 | | 2907 |
| AAC AAG GAA GAG AAA TG AGGATCTCAG GACCTTGGTG ACACTGTGT<br>Asn Lys Glu Glu Lys<br>925 | | 2954 |
| ACACCTCTGG ATTCATTGTC TCTCACAGAT GTGACTGTAT | | 2994 |

(2) INFORMATION FOR SEQ ID NO:5:

(i) SEQUENCE CHARACTERISTICS:
        (A) LENGTH: 928 amino acids
        (B) TYPE: amino acid
        (D) TOPOLOGY: linear (ii) MOLECULE TYPE: protein (xi) SEQUENCE DESCRIPTION: SEQ ID NO:5:

Met Pro Pro Lys Thr Pro Arg Lys Thr Ala Ala Thr Ala Ala Ala Ala
1                5                    10                  15

```
Ala Ala Glu Pro Pro Ala Pro Pro Pro Pro Pro Glu Asp
            20              25              30
Pro Glu Gln Asp Ser Gly Pro Glu Asp Leu Pro Leu Val Arg Leu Glu
                35              40              45
Phe Glu Glu Thr Glu Glu Pro Asp Phe Thr Ala Leu Cys Gln Lys Leu
         50              55              60
Lys Ile Pro Asp His Val Arg Glu Arg Ala Trp Leu Thr Trp Glu Lys
 65              70              75              80
Val Ser Ser Val Asp Gly Val Leu Gly Gly Tyr Ile Gln Lys Lys
                85              90              95
Glu Leu Trp Gly Ile Cys Ile Phe Ile Ala Ala Val Asp Leu Asp Glu
                100             105             110
Met Ser Phe Thr Phe Thr Glu Leu Gln Lys Asn Ile Glu Ile Ser Val
            115             120             125
His Lys Phe Phe Asn Leu Leu Lys Glu Ile Asp Thr Ser Thr Lys Val
            130             135             140
Asp Asn Ala Met Ser Arg Leu Leu Lys Lys Tyr Asp Val Leu Phe Ala
145             150             155             160
Leu Phe Ser Lys Leu Glu Arg Thr Cys Glu Leu Ile Tyr Leu Thr Gln
                165             170             175
Pro Ser Ser Ser Ile Ser Thr Glu Ile Asn Ser Ala Leu Val Leu Lys
                180             185             190
Val Ser Trp Ile Thr Phe Leu Leu Ala Lys Gly Glu Val Leu Gln Met
            195             200             205
Glu Asp Asp Leu Val Ile Ser Phe Gln Leu Met Leu Cys Val Leu Asp
            210             215             220
Tyr Phe Ile Lys Leu Ser Pro Pro Met Leu Leu Lys Glu Pro Tyr Lys
225             230             235             240
Thr Ala Val Ile Pro Ile Asn Gly Ser Pro Arg Thr Pro Arg Arg Gly
                245             250             255
Gln Asn Arg Ser Ala Arg Ile Ala Lys Gln Leu Glu Asn Asp Thr Arg
            260             265             270
Ile Ile Glu Val Leu Cys Lys Glu His Glu Cys Asn Ile Asp Glu Val
            275             280             285
Lys Asn Val Tyr Phe Lys Asn Phe Ile Pro Phe Met Asn Ser Leu Gly
            290             295             300
Leu Val Thr Ser Asn Gly Leu Pro Glu Val Glu Asn Leu Ser Lys Arg
305             310             315             320
Tyr Glu Glu Ile Tyr Leu Lys Asn Lys Asp Leu Asp Ala Arg Leu Phe
                325             330             335
Leu Asp His Asp Lys Thr Leu Gln Thr Asp Ser Ile Asp Ser Phe Glu
            340             345             350
Thr Gln Arg Thr Pro Arg Lys Ser Asn Leu Asp Glu Glu Val Asn Val
            355             360             365
Ile Pro Pro His Thr Pro Val Arg Thr Val Met Asn Thr Ile Gln Gln
            370             375             380
Leu Met Met Ile Leu Asn Ser Ala Ser Asp Gln Pro Ser Glu Asn Leu
385             390             395             400
Ile Ser Tyr Phe Asn Asn Cys Thr Val Asn Pro Lys Glu Ser Ile Leu
            405             410             415
Lys Arg Val Lys Asp Ile Gly Tyr Ile Phe Lys Glu Lys Phe Ala Lys
            420             425             430
```

```
Ala Val Gly Gln Gly Cys Val Glu Ile Gly Ser Gln Arg Tyr Lys Leu
        435                 440                 445

Gly Val Arg Leu Tyr Tyr Arg Val Met Glu Ser Met Leu Lys Ser Glu
    450                 455                 460

Glu Glu Arg Leu Ser Ile Gln Asn Phe Ser Lys Leu Leu Asn Asp Asn
465                 470                 475                 480

Ile Phe His Met Ser Leu Leu Ala Cys Ala Leu Glu Val Val Met Ala
                485                 490                 495

Thr Tyr Ser Arg Ser Thr Ser Gln Asn Leu Asp Ser Gly Thr Asp Leu
            500                 505                 510

Ser Phe Pro Trp Ile Leu Asn Val Leu Asn Leu Lys Ala Phe Asp Phe
        515                 520                 525

Tyr Lys Val Ile Glu Ser Phe Ile Lys Ala Glu Gly Asn Leu Thr Arg
    530                 535                 540

Glu Met Ile Lys His Leu Glu Arg Cys Glu His Arg Ile Met Glu Ser
545                 550                 555                 560

Leu Ala Trp Leu Ser Asp Ser Pro Leu Phe Asp Leu Ile Lys Gln Ser
                565                 570                 575

Lys Asp Arg Glu Gly Pro Thr Asp His Leu Glu Ser Ala Cys Pro Leu
            580                 585                 590

Asn Leu Pro Leu Gln Asn Asn His Thr Ala Ala Asp Met Tyr Leu Ser
        595                 600                 605

Pro Val Arg Ser Pro Lys Lys Lys Gly Ser Thr Thr Arg Val Asn Ser
    610                 615                 620

Thr Ala Asn Ala Glu Thr Gln Ala Thr Ser Ala Phe Gln Thr Gln Lys
625                 630                 635                 640

Pro Leu Lys Ser Thr Ser Leu Ser Leu Phe Tyr Lys Lys Val Tyr Arg
                645                 650                 655

Leu Ala Tyr Leu Arg Leu Asn Thr Leu Cys Glu Arg Leu Leu Ser Glu
            660                 665                 670

His Pro Glu Leu Glu His Ile Ile Trp Thr Leu Phe Gln His Thr Leu
        675                 680                 685

Gln Asn Glu Tyr Glu Leu Met Arg Asp Arg His Leu Asp Gln Ile Met
    690                 695                 700

Met Cys Ser Met Tyr Gly Ile Cys Lys Val Lys Asn Ile Asp Leu Lys
705                 710                 715                 720

Phe Lys Ile Ile Val Thr Ala Tyr Lys Asp Leu Pro His Ala Val Gln
                725                 730                 735

Glu Thr Phe Lys Arg Val Leu Ile Lys Glu Glu Glu Tyr Asp Ser Ile
            740                 745                 750

Ile Val Phe Tyr Asn Ser Val Phe Met Gln Arg Leu Lys Thr Asn Ile
        755                 760                 765

Leu Gln Tyr Ala Ser Thr Arg Pro Pro Thr Leu Ser Pro Ile Pro His
    770                 775                 780

Ile Pro Arg Ser Pro Tyr Lys Phe Pro Ser Ser Pro Leu Arg Ile Pro
785                 790                 795                 800

Gly Gly Asn Ile Tyr Ile Ser Pro Leu Lys Ser Pro Tyr Lys Ile Ser
                805                 810                 815

Glu Gly Leu Pro Thr Pro Thr Lys Met Thr Pro Arg Ser Arg Ile Leu
            820                 825                 830

Val Ser Ile Gly Glu Ser Phe Gly Thr Ser Glu Lys Phe Gln Lys Ile
        835                 840                 845

Asn Gln Met Val Cys Asn Ser Asp Arg Val Leu Lys Arg Ser Ala Glu
    850                 855                 860
```

```
Gly Ser Asn Pro Pro Lys Pro Leu Lys Lys Leu Arg Phe Asp Ile Glu
865             870             875             880

Gly Ser Asp Glu Ala Asp Gly Ser Lys His Leu Pro Gly Glu Ser Lys
            885             890             895

Phe Gln Gln Lys Leu Ala Glu Met Thr Ser Thr Arg Thr Arg Met Gln
            900             905             910

Lys Gln Lys Met Asn Asp Ser Met Asp Thr Ser Asn Lys Glu Glu Lys
        915             920             925
```

RETINOBLASTOMA GENE-CANCER SUPPRESSOR AND REGULATOR

This application is a continuation of Ser. No. 07/951947, filed Sep. 28, 1992, which is a continuation of Ser. No. 07/108,748 filed Oct. 15, 1987.

This invention was made with Government support under Grant No.: EY 05758 with the National Institutes of Health and the University of California. The Government has certain rights in this invention.

FIELD OF THE INVENTION

This invention relates in general to a genetic control of retinoblastoma and regulation of carcinogenicity. In particular this invention relates to the cloning, isolation, identification and sequencing of the retinoblastoma gene. The invention also relates to the method of use of the cloned retinoblastoma gene cDNA as a tool for diagnosing retinoblastoma, osteosarcoma and fibrosarcoma. Finally, the invention relates to the gene therapy that replaces the defective gene in cancer cells with normal gene which should suppress cancer formation.

BACKGROUND

A proposed general hypothesis of carcinogenesis consists of the following features: All cells possess multiple structural genes capable of coding for transforming factors which can release the cell from its normal constraints on growth. In adult cells, these structural genes are suppressed by diploid pairs of regulatory genes and some of the transforming genes are tissue specific. The structural genes loci are temporarily activated at some stage of embryogenesis and possibly during some stage of the cell cycle in adult cells. Spontaneous tumors, or tumors induced by chemicals or radiation, arise as the result of mutations of any set of regulatory genes releasing the suppression of the corresponding structural genes and leading to transformation of the cell. Autosomal dominant hereditary tumors, such as retinoblastoma, are the result of germ-line inheritance of one inactive regulatory gene. Subsequent somatic mutation of the other regulatory gene leads to tumor formation. *Proc. Natl. Acad. Sci.*, 70:3324–3328 [1973]

Thus, under the above theory, it seems entirely plausible that cancer such as retinoblastoma may result when specific genes regulating certain types of cells are activated or inactivated. On the other hand, from the other available evidence outlined below, it is equally plausible that the retinoblastoma gene itself acts as one of the regulatory genes involved in tumorigenesis of certain tissues.

Retinoblastoma tumors have been associated with an interstitial deletions of the long arm of chromosome 13. The deletion of a specific locus on chromosome 13 would be followed by somatic mutation with the consequence of tumor formation. (Ibid).

Thus, the retinoblastoma tumor is a prototypic model for the study of genetic determination of cancer. *Amer. J. Hum. Genet.*, 30:406–421 [1978].

Retinoblastoma, the most common intraocular cancer of childhood, occurs in both hereditarily and nonhereditarily acquired forms. The former is characterized by early age onset and multiple tumor foci compared to the nonhereditary type, which occurs later on with a single, unilateral tumor. *Proc. Natl. Acad. Sci.*, 68:820–822 [1971]; *Hum. Gen.*, 52:1–67 [1979]; and *Science*, 223:1028–1033 [1984].

Retinoblastoma is a malignant embryonal tumor of the sensory layer of the retina that arises in the retina of one eye (unilateral) or both eyes (bilateral), and it is frequently multicentric. Retinoblastomas are characterized by small round cells with deeply staining nuclei, and elongated cells forming rosettes. They usually cause death by local invasion, especially along the optic nerves. The molecular mechanism of the formation of this tumor is unknown.

Although most retinoblastoma ("RB") patients survive the disease, the consequences of undiagnosed and untreated retinoblastoma are severe. Therefore, an understanding of the genetic aspects and early diagnosis of this disease is very important. Without the isolation, identification and sequencing of the RB gene, such understanding and early diagnosis is very difficult.

Retinoblastoma occurs unilaterally in about 65% of cases and bilaterally in the remaining 35%. The majority of patients have a negative family history for this tumor. Despite this, it has been estimated that 40% of the patients, including all of those with bilateral disease, have a hereditary basis to their tumor. The genetic form of retinoblastoma demonstrates the characteristic features of hereditary cancers. Children having retinoblastoma at an earlier age average up to 9–10 months, usually have bilateral disease. *Gen Cytogen*, 58:534–540 [1986].

The pattern of inheritance is autosomal dominant, with a risk of 50% that the child of an affected parent will receive the gene for retinoblastoma, and a 90% chance that he or she will manifest the tumor. There is an increased risk for the development of second primary malignancies, particularly osteogenic sarcoma and fibroblastoma, both within and outside the field of radiation therapy. Molecular genetic evidence has been reported that the development of retinoblastoma and osteosarcoma involves the specific somatic loss of constitutional heterozygosity for the region of human chromosome 13 which includes the RB 1 locus. *Proc. Natl. Acad. Sci*, 82:6216–6220 [1985].

In addition, the same cancers that occur frequently as second primary tumors in patients with hereditary retinoblastoma have been observed in their relatives.

Two-mutation hypothesis explains the occurrence of retinoblastoma in both a hereditary and a sporadic form with differing frequencies of bilaterality. It proposes that all retinoblastomas occur as a result of two mutational events. In the hereditary form the first mutation is germinal, and thus is present in all cells of the individual. Only a single second mutation in the somatic target cell is required for development of the tumor. Therefore, these tumors might be expected to occur at an early age and to be bilateral. In the nonhereditary form, both mutations take place post-zygotically in the same somatic cell, and thus, these tumors would more likely be unilateral and occur at a relatively later age. Cytogenetic and molecular genetic studies of patients with retinoblastoma have provided data that strongly support this hypothesis.

Susceptibility to hereditary retinoblastoma is transmissible to offspring as an autosomal-dominant trait from parent to child with 90% penetrance. Under the above hypothesis, the inherited gene alone is not sufficient for carcinogenesis because not everyone who receives it develops the cancer, and not every susceptible cell carrying it becomes transformed. Thus, another event, a second gene change, or "second hit" such as deletion or rearrangement of the gene, is necessary.

The retinoblastoma gene deletions have been directly linked to the retinoblastoma. *JNCI*, 71:1107–1114 [1983].

A constitutional chromosome abnormality in a patient with retinoblastoma, with a deletion of one of the D group chromosomes, was previously reported. The D group chromosome involved in retinoblastoma cases is chromosome 13, and the band common to all the deletions is 13q14. These data suggested that the retinoblastoma gene is located within this chromosomal band.

Gene dosage studies have demonstrated that the locus for the enzyme esterase D is also located in band 13q14, and is closely linked to the retinoblastoma gene. Thus, there is available a biochemical marker for small deletions of this region of chromosome 13. Most of the patients with this specific chromosomal deletion have other phenotypic abnormalities in addition to retinoblastoma. Although there is no classical phenotype, developmental delay, microcephaly, microphthalmia, and skeletal and genitourinary malformations have been reported.

The patients with constitutional deletions of chromosome band 13q14 clearly demonstrate the first germinal mutation. Evidence for a second somatic cell mutation has recently been published in Nature, 305:779–784 [1983]. Restriction fragment length polymorphisms were used to compare constitutional and tumor genotypes of patients with retinoblastoma. The results suggest that tumorigenesis may result from the development of homozygosity for a recessive mutant allele at the retinoblastoma locus. In other words, the patients inherited one mutant allele, and homozygosity occurred when the normal allele was lost by mitotic non-disjunction or mitotic recombination. Thus, although pedigree analyses of families with hereditary retinoblastoma are compatible with an autosomal dominant pattern of inheritance, molecular genetic studies support the hypothesis that the retinoblastoma locus is recessive, and that both alleles must undergo mutation before the tumor is expressed. Gen. Cytogen., 58:534–540 [1986].

The genetic locus determining retinoblastoma susceptibility was assigned to band q14 of chromosome 13, along with the gene for the polymorphic marker enzyme esterase D ("ESD"), by examination of cytogenetic deletions. Science, 208:1042–1044 [1980]. The close linkage of these loci was confirmed by studies of retinoblastoma pedigrees. Science, 219:971–972 [1983].

The retinoblastoma susceptibility locus was further implicated in nonhereditary retinoblastoma by observations of frequent chromosome 13 abnormalities in tumor karyotypes and reduced esterase D activity in tumors. Cancer Genet. Cytogenet., 10:311–333 [1983].

The proposition has been made previously that inactivation of both alleles of the RB gene located in region 13q14 evidenced by the reduced esterase D activity resulted in retinoblastoma. Such proposition was based in part on a case of hereditary bilateral retinoblastoma LA-RB69 in which both RB alleles located in close proximity of the esterase D gene were inferred to be absent. Science, 219:973–975 [1983]. Recently, however, the assumption that the absence of esterase D activity implied loss of both esterase D and RB genes has been disproved by finding a low but detectable quantity of esterase D protein and enzymatic activity present in tumor cells LA-RB69. Hum. Genet., 76:33–36 [1987].

Nonetheless, Cavenee et al., (Nature, 305:779–784 [1983]) found that chromosome 13 markers that were heterozygous in somatic cells often became homozygous or hemizygous in retinoblastoma tumors. Homozygous 13q14 deletions at the molecular level in 2 out of 37 retinoblastoma tumors were also reported in Proc. Natl. Acad. Sci, 83:7391–7394 [1986]. These experiments provided evidence that the proposed RB gene may function in a "recessive" manner at the cellular level, in distinction to the "dominant" activities of classical oncogenes as measured, for example, by transfection assays. Science, 235:305–308 [1987] and Cancer Res., 46:1573–1580 [1986].

Thus, absence or inactivation of the RB gene, mapped to the chromosome 13q14:11 region, is believed to be the primary cause of retinoblastoma. Science, 213:1501–1503 (1981), Science, 223: 1028–1033 (1984), Proc. Natl. Acad. Sci., 68:820–823 (1971), Nature, 305:779–784 (1980). Since little of the RB gene structure or function is known, its cloning has proved to be difficult. Discover, March:85–96 (1987).

There is now enough evidence available showing the genetic involvement in the development of retinoblastoma and its secondary tumors. However, the precise location of the RB gene, its identification, isolation and nucleotide sequence and cloning, as well as the amino acid sequence of its protein product, is necessary for early diagnosis and treatment but difficult to obtain. It would be therefor advantageous to have this information available to enable the development of diagnostic procedure and treatment.

The latest reports suggest that the RB gene may have a regulatory function and that its presence and normal function prevents the development of the retinoblastoma. On the other hand, absence, malfunctioning or inactivation of the RB gene causes the development of, or genetical predisposition and susceptibility, to the retinoblastoma and is believed to be the primary cause for both hereditary and acquired retinoblastoma, osterosarcoma and fibroblastoma and other cancers.

Therefore, to find a way of determining the genetic predisposition in the fetus or the susceptibility in later age of acquiring retinoblastoma, by determination of the normal or abnormal function of the RB gene, is of utmost importance for early diagnosis and/or possible treatment of retinoblastoma, ostesarcoma, fibroblastoma and other cancers through a genetic manipulation.

The research on genetics of the retinoblastoma has a long history. Discover, March:85–96 [1987]. The major turn in retinoblastoma occured in early 1980 when general radioactive DNA probes were prepared against specific regions of chromosome 13. These probes were instrumental in findings that the retinoblastoma patients have abnormalities at 13q14 region of chromosome 13. Am. J. Hum. Genet., 36:10–24 [1984].

The next important finding of the esterase D gene location in the close proximity of the retinoblastoma gene was made in 1984. Then walking along the chromosome from the esterase D gene was initiated, including the cloning, probing, and screening. This approach eventually led to the identification, isolation and sequencing of the RB gene as disclosed in this invention. Science, 235:1394–1399 [1987].

Independently, there were other attempts to isolate RB gene by preparation and random use of DNA probes for the q14 region, using cells from the eye tissue of a fetal eye and from the retinoblastoma tumor. This random approach resulted in the finding of two tumor cells of 2 retinoblastoma patient missing part of the chromosome 13. Apparently at least a fragment of the gene was identified by one of the randomly constructed and used DNA probes. Later on, it was determined that the fragment was expressed in normal fetal eye tissue but was not expressed in retinoblastoma. Although scientists at that point called the results a detection of the gene, there was, and still is not sufficient evidence available that the whole gene was indeed identified at that time. The discovered fragment was later cloned. Discover, March:85–96 [198].

Since the discoveries of the RB gene fragment, published in *Nature,* Vol.323:643–646 [1986], only disclosed the randomly obtained but not identified and sequenced piece of DNA, albeit probably a portion of the RB gene, it would be greatly advantageous to identify the exact nucleotide sequence of the whole RB gene, including the initiation and termination codons to identify the amino acid sequence of the retinoblastoma gene protein product and to provide the antibody against such protein. The specific anti-RB protein antibody would be usable as the diagnostic tool in diagnosing retinoblastoma and other secondary cancers associated therewith and for regulation of carcinogenicity.

The localization of esterase D and RB genes in the same chromosomal region provides an advantageous approach for evaluation of RB gene functioning, for discovery of RB chromosomal patterns, for cloning of the RB gene, for isolating the RB gene and identifying the RB gene sequence by chromosomal walking, using the esterase D cDNA clone as the starting point. The isolation, identification and cloning of esterase D was part of the current discovery and is the subject of pending U.S. patent application Ser. No. 091547 filed on Aug. 31, 1987, hereby incorporated by reference. The protein product of the RB gene, namely phosphoprotein ppRB$^{110}$, was isolated and its amino acid sequence determined as a part of this invention. It is independently disclosed and claimed in copending U.S. patent application Ser. No. 098612, filed on Sep. 17, 1987, and is hereby incorporated by reference. The subject matter was also published in *Proc. Natl. Acad. Sci.,* 83:6337–6341 and 6790–6794 (1986). *Science,* 235:1394–1399 (1987).

The identification of the exact RB gene location, isolation, identification, sequencing and cloning of the RB gene; the identification of the RB protein, and preparation of the specific anti-RB antibody would allow diagnosis and treatment of the retinoblastomas and their secondary tumors and other cancers regulated completely or partially by the RB gene.

It is therefore one object of this invention to identify and isolate the RB gene.

It is another object of this invention to determine the exact nucleotide sequence of the cloned RB cDNA derived from RB gene.

It is yet another object of this invention to prepare RB cDNA and to clone the same.

It is a further object of this invention to prepare appropriate RB gene probes.

It is a further object of this invention to provide a method for diagnosing a retinoblastoma and its related secondary cancers and susceptibility thereto and to provide treatment of retinoblastoma by genetic manipulation.

It is still a further object of this invention to provide a method for diagnosing a tumorigenicity of tissue regulated by the RB gene.

DISCLOSURE OF INVENTION

During the last four years, the subject of this invention was thoroughly and laboriously investigated. The esterase D gene was located, identified, sequenced and cloned. Specific esterase D clone EL22 together with another probe H3–8 were mapped to the same chromosome region 13q14 as is the known location of the RB gene.

Bidirectional chromosomal walking along the chromosome 13 DNA was instituted using alternatively the clones of genomic DNA and cDNA as probes. This alternative screening led to the identification of several distinct clones such as SD-1, SD-2, RB-1, RB-2 and RB-5. Clones SD1 and SD-2 were isolated by means of H 1.2 probes. Clones RB-1, RB-2 and later on discovered RB-5 were isolated by means of H1.3 probe. Clone RB-1 of 1.6 kb and RB-2 clone of 0.9 kb were found to be overlapping. Clone RB-5 with an insert of 3.5 kb is partially overlapping with clone RB-1 in a 0.4 kb region.

Candidate RB gene were used as probes in RNA blotting to detect mRNA transcripts and clones RB-1 and RB-5 were hybridized with a 4.6 kb mRNA fragment obtained from the normal retinal and placental tissues. Hybridization under the same conditions with mRNA obtained from the retinoblastoma mRNA transcripts was not observed at all.

Other type of tumors not related to retinoblastoma, namely neuroblastoma and medulloblastoma, displayed normal 4.6.kb mRNA transcripts.

Two cDNA libraries, placental and fetal retina, were rescreened with clone RB-1 for complete cDNA clone and resulted in the isolating of clone RB-5.

Additional probes were generated by cleaving RB-1 clone with EcoRI into 0.9 kb (RB0.9) and 0.7 kb (RB0.7 kb) fragments. RB-5 was cleaved by BglII into three fragments called RB710 (0.7 kb, EcoRI-BglII), RB1.8 kb (1.8 kb? BglII-BglII) and RB1.0 (1.0 kb, BglII-EcoRI).

The mRNA transcripts orientation was determined by generating single-stranded M13 clones from both strands of RB 1.8. RNA blotting analysis using M13 clones as probes has shown that the DNA sense strand runs form 5' to 3' from the 0.9 kb fragment of RB-1 to the 1.0 kb fragment of RB-5.

Genomic DNA encoding for the RB gene from retinoblastoma tumor cells was studied by hybridization in DNA blotting analysis with probes RB-5 and RB 0.9. It discovered numerous large Hind III bands suggesting that the RB locus was spread over a large genomic region.

Additionally, more than 20 phage clones were isolated from a human genomic DNA library with RB-1 and RB-5 as probes and were subsequently characterized by restriction mapping and hybridization to subfragment cDNA probes. The Hind III restriction map of the RB gene was then constructed showing that the RB gene consists of at least 12 exons scattered over more than 100 kb of DNA.

The sequence analysis was performed and yielded the reconstructed complete cDNA sequence. Deletion templates were generated which yielded greater than 95% of the sequence.

The sequence of the RB gene protein products was then predicted and an amino acid-hydropathy plot constructed.

The phylogenetic developmental functions of the RB gene and the evolutionary conservation of the RB gene in vertebrates were investigated and disclosed RB-gene homologous sequences in all investigated species.

Expression of retinoblastoma and c-fos genes in human osteosarcoma and fibroblastoma was investigated. Most osteosarcoma cell lines (five of six) expressed normal 4.6 kb mRNA, while one had a shortened mRNA transcript with an internal deletion. Fibrosarcoma expressed an abnormal RB mRNA transcript 6.5 kb in length without apparent DNA abnormality. Expression of c-fos was found in all osteosarcoma tumors but not in osteosarcoma cell lines or in fibrosarcoma.

Through the above outlined experimental design, a gene encoding a messenger RNA (mRNA) of 4.6 kilobases (kb), located in the proximity of esterase D, was identified as the retinoblastoma susceptibility gene on the basis of chromosomal location, homozygous deletion, and tumor-specific alterations in expression. Transcription of this gene was abnormal in six of six retinoblastomas examined: in two tumors, RB mRNA was not detectable, while four others expressed variable quantities of RB mRNA with decreased molecular size of about 4.0 kb. In contrast, full-length RB mRNA was present in human fetal retina and placenta tumors, and in other tumors such as neuroblastoma and medulloblastoma. DNA from retinoblastoma cells had a homozygous gene deletion in one case and hemizygous deletion in another case, while the remainder were not grossly different from normal human control DNA.

The RB gene contains 24 exons distributed in a region of over 150 kb. Sequence analysis of complementary DNA clones yielded a single long open reading frame that could encode a hypothetical protein of 928 amino acids [*Nature,* in press]. A computer-assisted search of a protein sequence database revealed no closely related proteins. Features of the predicted amino acid sequence included potential metal-binding domains similar to those found in nucleic acid-binding proteins. These results suggest involvement of the RB gene as a recessive genetic mechanism for regulation of human cancers.

The initial starting point was the gene encoding esterase D which is linked to the retinoblastoma susceptibility locus in band 13q14.11 (*Proc. Natl. Acad. Sci.,* 83:6337–6341 [1986]) within an estimated 1500-kilobase range. The esterase D complementary DNA (cDNA) clone EL-22 was used as a probe to isolate its genomic DNA clones. Distal DNA segments of these genomic clones were used to isolate additional genomic clones. At 20-kb intervals in walking regions, unique sequences were identified that were used as probes to isolate cDNA clones from fetal retina and placenta libraries. A bidirectional chromosome walk covering 120 kb (FIG. 1) have been established by alternately screening genomic and cDNA libraries.

Two cDNA clones, SD-1 and SD-2, were isolated by means of probes 5' to the esterase D gene. Chromosome walking 3' to the esterase. D gene was hampered by a 20-kb region containing highly repetitive sequences. Additional probe H3–8 was isolated by random selection from a chromosome 13-specific genomic library (*Cancer Gen. Cytogen.,* 13:283–289 [1984]). Preliminary results with orthogonal field gel electrophoresis indicated that H3–8 was less than 500 kb from the esterase D gene. Starting from the location of H3–8, a second bidirectional chromosome walk was performed in a manner similar to that above, extending over 30 kb. A unique DNA fragment H-1.2 identified two overlapping cDNA clones of 1.6 kb (RB-1) and 0.9 kb (RB-2) in human cDNA libraries (FIG. 1).

Candidate RB genes were used as probes in RNA blotting analysis to detect relevant messenger RNA (mRNA) transcripts (Table 1). Polyadenylated RNA was prepared from human fetal retinas (obtained by dissection of about 25 first- or second- trimester fetal eyes) and from portions of normal human placentas. Since the primary retinoblastoma tumor samples large enough to yield sufficient mRNA for analysis are not usually available, polyadenylated RNA was isolated from cultured cells of six retinoblastomas. Additionally, polyadenylated RNA was isolated from three neuroblastomas and one medulloblastoma and from a primary medulloblastoma specimen.

Esterase D transcripts (1.4 kb) were detected in all tumor and tissue samples (FIG. 2). This finding was consistent with the known "constitutive" expression of esterase D. Esterase D hybridization was subsequently used as a positive control.

Clones SD-1 and SD-2 were isolated by means of probes 5' to the esterase D gene. Neither SD-1 nor SD-2 seemed promising as candidate RB genes, because transcripts hybridizing to these clones were not detected in retina or placenta mRNA samples nor in samples from any retinoblastomas (Table 1). Since SD-1 and SD-2 were obtained from placental and fetal retinal cDNA libraries, respectively, their expression in cognate mRNA was expected. Thus both SD-1 and SD-2 might be expressed at very low level and cannot be detected by the RNA blotting.

RB-1 hybridized with a 4.6-kb mRNA transcript in fetal retina and placenta (FIG. 2). In three of six retinoblastoma samples (FIG. 2A, lanes 1, 2, and 5), abnormal mRNA transcripts measuring approximately 4.0 kb were detected by RB-1. In three retinoblastomas (FIG. 2A, lanes 3, 4 and 6), mRNA transcripts were not observed. Results from retinoblastoma samples 3, 4, and 6 were duplicated by overloading lanes and prolonged autoradiographic exposure, confirming that mRNA transcripts were indeed absent in tumors 3, 4 and 6. Esterase D mRNA was detected in all cases.

Three neuroblastomas and two medulloblastomas displayed identical transcripts of 4.6 kb, equivalent to that in normal tissues (FIG. 2B). Altered RB-1 related gene expression (manifested as a shortened transcript or absence of transcript) was thus found in six of six retinoblastomas, but not in two normal tissues or two other related human tumors of neurectodermal origin, strongly suggesting that RB-1 represented part of the putative RB gene.

A complete cDNA clone was sought by rescreening the two cDNA libraries with RB-1 as probe. Clone RB-5, with a 3.5 kb insert, was isolated. It gave identical results as RB-1 in mRNA hybridization.

Restriction enzyme analysis suggested that RB-5 and RB-1 overlapped in a 0.4 kb region, and together defined a DNA segment of about 4.6 kb, a size close to that of the normal mRNA transcript. For ease of analysis, the following probes were generated: RB-1 was cleaved by Eco RI into 0.9 kb (RB0.9) and 0.7 kb (RB0.7) fragments. RB-5 was cleaved by Bgl II into three fragments called RB710 (0.7 kb, Eco RI-Bgl II), RB1.8 (1.8 kb, Bgl II-Bgl II), and RB1.0 (1.0 kb, Bgl II-Eco RI).

The mRNA transcript orientation was determined by generating single-stranded M13 clones from both strands of RB1.8, which were then used as probes in RNA blotting analysis. The results indicated that the DNA sense strand runs 5' to 3' from the 0.9 kb fragment of RB-1 to the 1.0-kb fragment of RB-5.

It was believed that some alterations in mRNA expression or size might be due to small deletions in genomic DNA encoding the candidate RB gene. Consequently, genomic DNA was extracted from corresponding tumor cells described for FIG. 2 digested with Hind III, and hybridized in DNA blotting analysis with probes RB-5 (FIG. 3A) and RBO.9 (FIG. 3B). Normal human genomic DNA was used as a control. Four of six retinoblastomas had genomic patterns identical to that of normal DNA. The RB gene was completely absent in sample 3. Decreased band intensities in DNA from sample 4 suggested the presence of a single copy of the RB gene, which was consistent with a cytogenetic feature of the tumor [del(13q12–q14)] as described in *Cancer Res,* 37:1003–1009 [1977]. Despite the absence of RB mRNA transcripts, genomic DNA from sample 6 was not detectably altered.

Thus only gross deletions but not small partial deletions of the RB gene were seen in these tumors, and detection of an intact genome did not imply normal gene expression. Such a disparity may be due to mutations in the promotor region. Explanations for decreased mRNA transcript size include small deletions within exons (which might not sufficiently alter gel mobility of large exon-containing Hind III fragments), or point mutations in exon splicing sequences or other mRNA processing signals.

The numerous large Hind III bands seen on DNA blotting analysis suggested that the RB locus was spread over a rather large genomic region. To further clarify genomic structure, more than 20 phage clones were isolated from a human genomic DNA library with RB-1 and RB-5 as probes (FIG. 4). These clones were characterized by restriction mapping and hybridization to subfragment cDNA probes. In conjunction with data from genomic DNA blotting (FIG. 3), the Hind III restriction map of the RB gene was constructed (FIG. 4). The RB gene consists of 24 exons scattered over more than 150 kb of DNA. One large intron of at least 20 kb is located between exons from the RB-1/RB-5 overlap region.

Recently described (Nature, 323:643–646 [1986]) was a cDNA clone with properties that were attributed to the RB gene. This clone detected a 4.7-kb mRNA transcript present in adenovirus 12-transformed retinal cells but absent in four of four retinoblastoma cell lines. Deletions involving part or all of this gene were observed in five retinoblastomas, but none of these were internal homozygous deletions. These findings were not sufficient to precisely identify the RB gene. Sequence data were not included in the report, the restriction map of the cDNA clone was similar to those found in this invention.

Genes with important developmental functions are often found to have similar counterparts in phylogenetically related organisms. We examined genomic DNA from five other vertebrate species by hybridizing with probe RB-5. Under standard hybridization stringencies, homologous sequences were detected in all samples, with weaker hybridization intensity as evolutionary distance increased (FIG. 5). The homologous chicken gene was just barely detectable. Thus the RB gene is measurably divergent in vertebrates, and may not be conserved in more distant species.

As noted above the RB gene expression, while specifically altered in retinoblastoma, was not confined to normal fetal retina but was also seen in at least one other normal unrelated tissue, placenta. For a more extensive survey, mRNA from fetal and adult rat tissues was prepared and analyzed by RNA blotting (FIG. 6). A 4.6-kb mRNA transcript (presumably the normal size for rat) was detected in all tissues, though quantity varied markedly. A second species of transcript, approximately 2.3 kb in size, was apparent in fetal rat brain. This short transcript may represent either differential processing of the RB gene or transcription of a separate but closely related gene.

Sequence analysis of clones RB-1 and RB-5 was performed by the dideoxy-terminator method of Sanger described in Proc. Natl. Acad. Sci., 74:5463–5467 [1977], to yield the reconstructed complete cDNA sequence (FIG. 7). Different deletion templates were generated by the "cyclone" method (Plasmid, 13:31–40 [1985]) in single-stranded M13 phage clones, which yielded greater than 95% of the sequence. The remaining gaps were sequenced by synthetic oligonucleotide primer on both strands. The complete sequence contained 4523 nucleotides, with a short poly(A) tail and a polyadenylation signal sequence (AATAA) near the 3' end. An open reading frame was present from the 5' end to base 2688, with numerous additional in-frame stop codons further downstream. Translation from the first methionine codon (base 241) yielded a hypothetical protein of 816 amino acids (98 kilo daltons in size).

Recently another RB cDNA clone was isolated that contained an additional 234 base pairs on the 5' end. The revised RB cDNA sequence had an additional methionine codon at nucleotide 139. When this methionine was used as initiation codon, the predicted RB protein had 928 amino acids and a molecular weight of 110 kD. The second in-frame methionine was at base 346. Since the nucleotide sequence surrounding at first ATG is not typical of other known mRNAs (23), the start codon assignment should be regarded as tentative. Later, the in vitro translation results favored the first methionine is the authentic initiation site. A computer search of the National Biological Research Foundation protein sequence database detected no strong homology with any of more than 4000 published amino acid sequences. However, a number of nucleic acid-binding proteins and viral proteins showed weak sequence homology, with a yeast DNA-directed RNA polymerase having the highest homology score.

The predicted protein sequence included ten potential glycosylation sites but a candidate transmembrane domain (at least 20 consecutive hydrophobic residues) was not found. The amino acid hydropathy plot showed a mildly hydrophobic region near the putative amino terminus and a hydrophilic region at the carboxyl terminus (FIG. 8). Two pairs of short amino acid sequences that were bracketed by cysteine and histidine residues in the manner of metal-binding domains found in nucleic acid-binding proteins were identified (FIG. 7). A region of 54 amino acids from position 663 to 716 contains 14 proline residues (26%). Such proline-rich regions have also been observed in nuclear oncogene proteins myc and myb. While the significance of these observations is not well established, they suggested that the RB gene product may be alnucleic acid-binding protein. Subsequently, the RB protein ppRB[110] has been found to be primarily located in cell nucleus.

The retinoblastoma gene has been previously found to be of a recessive nature. Tumor-specific alterations in gene expression provide the best evidence for identifying this gene as RB, and the examples of homozygous deletion and absence of mRNA expression support its postulated recessive nature.

Hereditary retinoblastoma patients have a high incidence of osteosarcoma as a second primary cancer. Inactivation of the retinoblastoma susceptibility (RB) gene has been implicated in the genesis of osteosarcoma by chromosomal homozygosity of the 13q14 region found in several osteosarcoma patients with or without retinoblastoma history. On the other hand, murine osteosarcoma-like tumors can be produced by viral vectors containing v-fos or "activated" c-fos oncogenes. To examine the inter-relationship of RB and fos genes, we have investigated expression of these genes in six human osteosarcoma cell lines, four fresh osteosaroma specimens, and one fibrosarcoma specimen. Among six osteosarcoma cell lines, one (SAOS2) expressed a shortened RB messenger RNA (mRNA) transcript with internal deletion of the RB gene; the remaining five cell lines expressed RB mRNA of normal size (4.6 kb) and had apparently normal RB gene structure. This was also the case for four fresh osteosarcoma specimens. Surprisingly, the fibrosarcoma expressed an abnormal RB mRNA transcript 6.5 kb in length without apparent DNA abnormalities. Expression of c-fos was found in all osteosarcoma tumors but was not detected in osteosarcoma cell lines or the fibrosarcoma tumor sample. The hypothesis that the RB gene product functions primarily to suppress c-fos gene expression was contradicted by cases in which presumably inactive RB genes were present without c-fos expression (SAOS2 and the fibrosarcoma), or in which RB genes appeared normal and c-fos expression was easily detected (all osteosarcoma tumors samples). These results suggest that 1) the RB gene may be involved in a variety of tumors other than retinoblastoma, 2) only a subset of osteosarcomas involve RB inactivation, and 3) the RB gene does not act primarily via regulation of the c-fos gene.

The RB gene is of more general interest than simply that attendant to a rare childhood cancer. First, recessive genes similar to RB may control other unusual embryonal childhood cancers such as nephroblastoma (Wilm's tumor), hepatoblastoma, embryonal rhabdomyosarcoma, and neuroblastoma. Like retinoblastoma, all of these tumors resemble massive overgrowth of tissues found in normal embryogenesis. Nephroblastoma has been associated with deletions of chromosome region 11p13, and adjacent polymorphic markers become homozygous in these tumors.

Since the sequence of the Rb gene is now known, the role of the RB gene in other tumors may now be explored. Retinoblastoma patients have a high rate of second malignancies occurring at a variety of sites; osteosarcome is the most common. Reduction to homozygosity in region 13q14 has been reported in osteosarcomas even without prior retinoblastoma, which suggests a common oncogenic mechanism for the two tumors despite their histologic and oncologic dissimilarity. In contrast, neuroblastoma and medulloblastoma, which are considered closely related to retinoblastoma, apparently do not involve alterations of RB. Further study of the RB gene will likely provide insight into unifying mechanisms of oncogenesis.

The identification, isolation, determination of the exact nucleotide sequence and cloning of the RB gene has a multiple utility.

The primary utility lies in the sequence transcription into its corresponding mRNA which is in turn translated into RB gene protein product. Protein product can then be used as an antigen in obtaining the specific anti-RB protein antibody. Antibody are then used as a diagnostic immunomarker for the investigation of the presence or absence of the RB gene protein in the examined tissue. If the RB protein is present, the RB gene is intact and retinoblastoma not present. If, on the other hand, the protein is absent or altered, the deficient RB gene is indicated and the resulting retinoblastoma or other cancers or susceptibility thereto is indicated.

The sequencing of the RB gene can be further utilized in producing the specific RB gene cDNA clones which can be used as the genetic markers and probes in isolation, identification and sequencing of other related genes or genes located in the proximity of the RB gene and of which function is as yet unknown.

The control and regulatory function of the RB gene is exerted through the RB protein which is instrumental in inhibiting other gene's oncogenic activity and restraining the malignant cell growth.

The presence or absence of the Rb gene will determine the presence or absence of the ppRB$^{110}$ which shall serve as a diagnostic tool in determination of presence or predisposition to retinoblastoma and other RB gene involved tumors. Such early diagnosis will allow an early warning and treatment of retinoblastoma and other tumors with the possibility of preventing development of the secondary tumors.

There are two approaches to utilize the current invention as a diagnostic tool for diagnosing retinoblastoma. The first one is to use the RB cDNA or genomic DNA as probes to determine the defect region of the mutated RB gene through genomic DNA blotting analysis or using the method of restriction fragment length polymorphism analysis to determine the diseased allele.

Alternatively, immunoscreening of the tissue biopsy with specific anti-ppRB$^{110}$ antibody is also practical. The bioptic tissue will be radioactively labeled with $^{35}$S-methionine, $^{32}$P-phosphoric acid or any other convenient radioisotope and immunoscreened, or the proteins extracted from bioptic tissue would be blotted on nitrocellulose filter and probed with labeled antibody according to method known in the art as Western blotting.

It is expected, that such readily available diagnostic methods will be used particularly for screening families with a history of hereditary retinoblastoma and for screening of their children.

The diagnostic method is also intended to be used for prophylactic prenatal and postnatal screening, and for prediction of the development of secondary cancer, such as osteosarcoma, fibrosarcoma, glioblastoma, breast cancer, etc., whether or not connected with retinoblastoma.

The other intended use is for suppression of tumorigenesis where the absent ppRB$^{110}$ will be provided through the molecular induction and gene transplanting of the RB cDNA to the individual in need of ppRB$^{110}$.

Still another use of the current invention is the suppression of the cancer growth providing RB gene cDNA directly to the tumor cells, which cells in turn will produce ppRB$^{110}$ which will affect the other tumorous cells.

BRIEF DESCRIPTION OF FIGURES AND DRAWINGS

FIG. 7 is the nucleotide and amino acid sequence of the RB gene.

FIG. 8 is the hydropathy plot of the amino acid sequence of the RB gene.

FIG. 9 is the chromatogram of RNA blot analysis of RB and c-fos gene in tumor cell lines and normal tissues.

FIG. 11A is the chromatogram of DNA blot analysis of genomic DNA fragments in osteosarcoma cell lines.

FIG. 11B is the drawing comparing the normal RB gene with a mutant allele of osteosarcoma cell line OAOS2.

DETAILED DESCRIPTION OF FIGURES AND DRAWINGS

Figure 1:
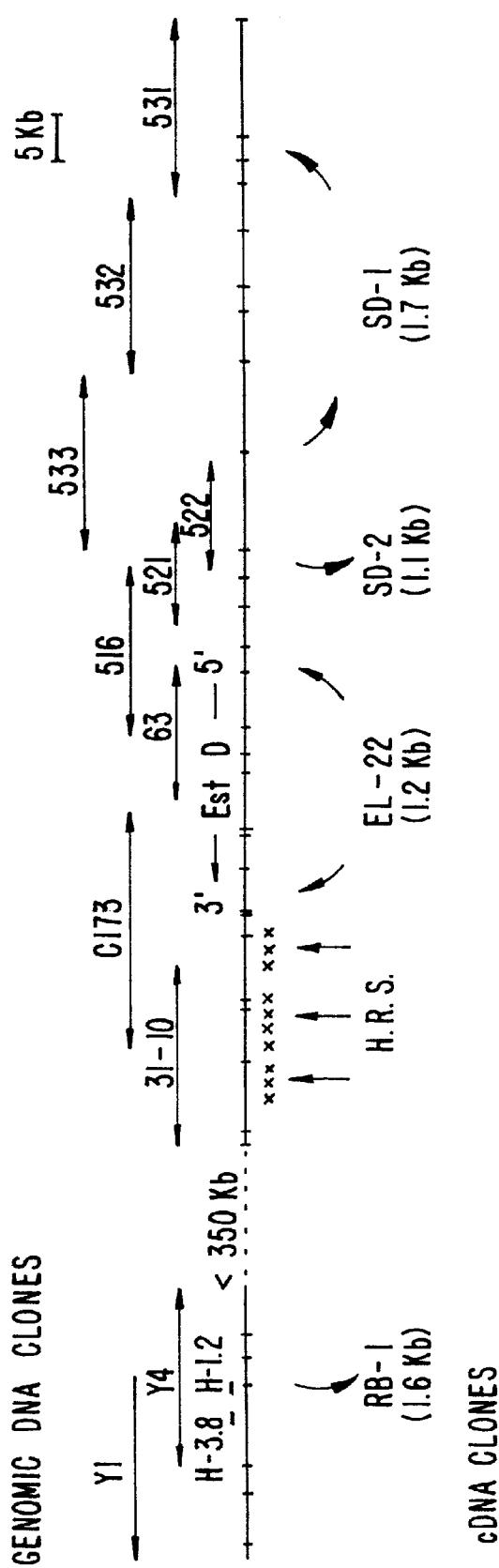
FIG. 1 is the drawing representing a summary of chromosomal walking.

FIG. 1 is the chromatogram summarizing the chromosome walking and isolation of cDNA clones from the 13g14 region. Starting points were EL-22 (the esterase D cDNA clone), located at 13q14.11, and H3–8, a 13q14-specific DNA probe. These probes were used to screen Charon 30, Charon 4A, EMBL-3, or cosmid genomic libraries from DNA of human peripheral blood lymphocytes or from DNA of Y79, a retinoblastoma cell line. Unique sequence subfragments of genomic clones were in turn used to screen λgt10 or gt11 cDNA libraries made from fetal retinal or placental mRNA, yielding SD-1, SD-2 and RB-1. Hybridization conditions were: 6×SSC/5 ×Denhardt's solution/ 0.1% SDS at 65° C. Washing conditions were: washed once in 2×SSC/0.1% SDS at room temperature for 15 minutes and twice in 0.2×SSC/0.1% SDS at 65° C. for 30 minutes. DNA fragments containing repetitive sequences were determined by hybridizing with $^{32}$P-labeled total human genomic DNA as probe. Those fragments failing to hybridize were considered unique sequence probes suitable for use in screening. Selected fragments were purified and labeled with α-$^{32}$P-dATP by nick translation or random oligonucleotide primer methods. The consensus map resulting from digestion with several restriction enzymes has the Eco RI sites shown. A 20-kb region 3' to the esterase D gene contained many highly repetitive sequences (H.R.S), since most restriction fragments from this region showed positive hybridization with either human Alu-1 probe or total genomic DNA. The maximal distance between H3–8 and EL-22 was determined by demonstrating a large Sal I-digested DNA fragment that hybridized with both probes, and the intergene separation was adjusted for distances already covered by chromosome walking.

Figures 2A, 2B:
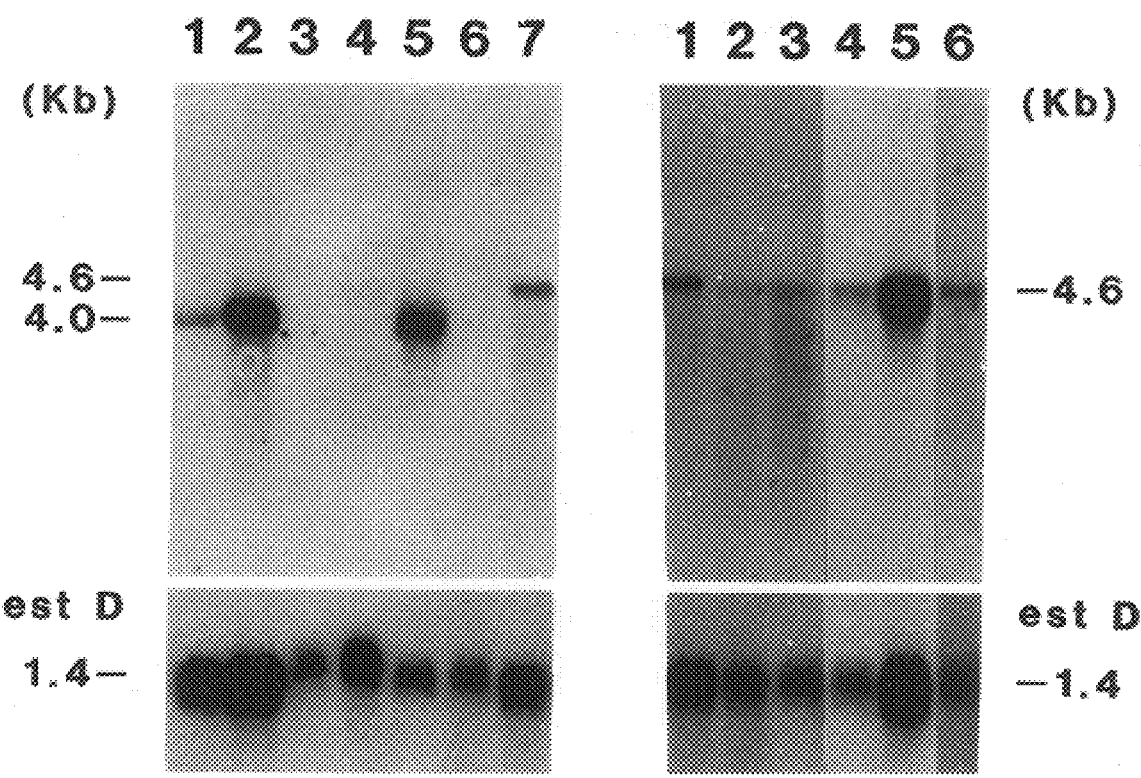
FIG. 2A is the chromatogram of RNA blot analysis of RB gene transcripts in retinoblastoma tumors and in normal fetal retina tissue.
FIG. 2B is the chromatogram of RNA blot analysis of RB gene transcripts in neuroblastoma cell lines, medulloblastoma cell line, medulloblastoma fresh tumor and normal tumor placenta.

FIG. 2A is the chromatogram showing the RNA blot analysis of RB gene transcripts in tumors and normal tissues. Polyadenylated RNA (2 to 5 μg) prepared form cultured retinoblastoma cells (lanes A1 to A6), fetal retina (lane A7), were separated by electrophoresis in 1% formaldehyde-agarose gels and transferred to nitrocellulose filters with 20×SSC. Filters were hybridized with $^{32}$P-labeled RB-1 DNA (top panel) in 50% formamide/6×SSC/5×Denhardt's solution/0.1% SDS/denatured salmon sperm DNA (100 μg/ml)/10 mM phosphate buffer (pH 7.0) at 42° C. for 24 hours. Washing followed 2×SSC/0.1% SDS at room temperature for 20 minutes and twice in 0.1×SSC/0.1% SDS at 65° for 30 minutes. Autoradiography was done with Kodak XAR-5 film at −70° C. for 3 days with an intensifying screen. Filters were then rehybridized with $^{32}$P-labeled EL-22 DNA as described above, and exposed for 3 days (bottom panel). The apparent slight variation in mobility of esterase D mRNA transcripts reflects the required overloading.

FIG. 2B is the chromatogram showing the RNA blot analysis of RB gene transcripts in tumors and normal tissues. Polyadenylated RNA (2 to 5 μg) prepared form cultured neuroblastoma cell lines (lanes B1 to B3), a medulloblastoma cell line and a fresh tumor (lanes B4 and B5), and human placenta (lane B6) were separated by electrophoresis in 1% formaldehyde-agarose gels and transferred to nitrocellulose filters with 20×SSC. Filters were hybridized with $^{32}$P-labeled RB-1 DNA (top panel) in 50% formamide/6× SSC/5×Denhardt's solution/0.1% SDS/denatured salmon sperm DNA (100 lg/ml)/10 mM phosphate buffer (pH 7.0) at 42° C. for 24 hours. Washing followed 2×SSC/0.1% SDS at room temperature for 20 minutes and twice in 0.1×SSC/ 0.1% SDS at 65° for 30 minutes. Autoradiography was done with Kodak XAR-5 film at −70° C. for 3 days with an intensifying screen. Filters were then rehybridized with $^{32}$P-labeled EL-22 DNA as described above, and exposed for 3 days (bottom panel). The apparent slight variation in mobility of esterase D mRNA transcripts reflects the required overloading.

Figure 3A:
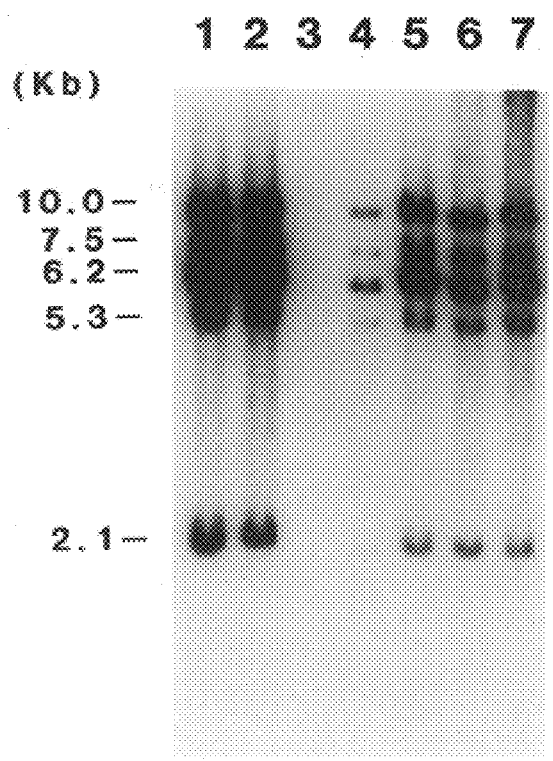
FIG. 3A is the chromatogram of DNA blot analysis of genomic DNA fragments in retinoblastoma tumors showing hybridization with $^{32}$P-labeled RB-5 DNA probe.

FIG. 3A is the chromatogram of the DNA blot analysis of genomic DNA fragments in retinoblastoma tumors. About 10 μg of DNA extracted from cultured cells derived from six retinoblastomas (lanes 1 to 6) and normal human DNA (lane 7) were digested with restriction enzyme Hind III, separated by electrophoresis in 0.75% agarose gels, and transferred to nitrocellulose filters with 10×SSC. Filters were hybridized with $^{32}$P-labeled RB-S DNA in 40% formamide/6×SSC/5× Denhardt's solution/0.1% SDS/denatured salmon sperm DNA (100μg/ml)/100 mM phosphate buffer (pH 7.0) at 42° for 24 hours. Filters were washed twice in 2×SSC/0.1% SDS at room temperature for 15 minutes and once in 0.2×SSC/ 0.1% SDS at 60° C. for 30 minutes. DNA quantitation was verified by washing filters at 95° C. to remove probes and then hybridizing as above with a $^{32}$P-labeled human growth hormone gene fragment. Band intensities indicated that lanes 5 to 7 had twice as much DNA as lane 4 and half as much DNA as lanes 1 to 3. With this adjustment, RB gene copy number was estimated at two for retinoblastoma samples 1,2,5, and 6, one for sample 4, and zero for sample 3.

Figure 3B:
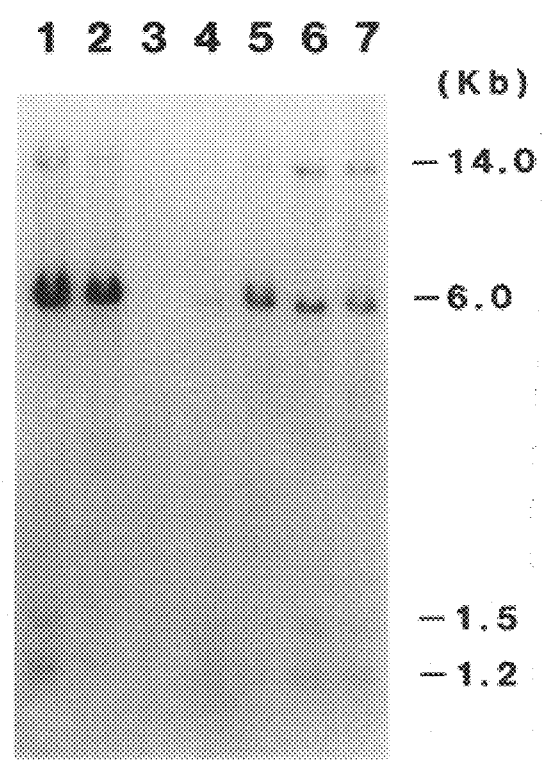
FIG. 3B is the chromatogram of DNA blot analysis of genomic DNA fragments in retinoblastoma tumors showing hybridization with $^{32}$P-labeled RB 0.9 DNA probe.

FIG. 3B is the chromatogram showing the DNA blot analysis of genomic DNA fragments in retinoblastoma tumors. About 10 μg of DNA extracted from cultured cells derived from six retinoblastomas (lanes 1 to 6) and normal human DNA (lane 7) were digested with restriction enzyme Hind III, separated by electrophoresis in 0.75% agarose gels, and transferred to nitrocellulose filters with 10×SSC. Filters were hybridized with $^{32}$P-labeled RB0.9 DNA in 40% formamide/6×SSC/5×Denhardt's solution/0.1% SDS/ denatured salmon sperm DNA (100 μg/ml)/100 mM phosphate buffer (pH 7.0) at 42° for 24 hours. Filters were washed twice in 2×SSC/0.1% SDS at room temperature for 15 minutes and once in 0.2×SSC/0.1% SDS at 60° C. for 30 minutes. DNA quantitation was verified by washing filters at 95° C. to remove probes and then hybridizing as above with a $^{32}$P-labeled human growth hormone gene fragment. Band intensities indicated that lanes 5 to 7 had twice as much DNA as lane 4 and half as much DNA as lanes 1 to 3. With this adjustment, RB gene copy number was estimated at two for retinoblastoma samples 1,2,5, and 6, one for sample 4, and zero for sample 3.

Figure 4:
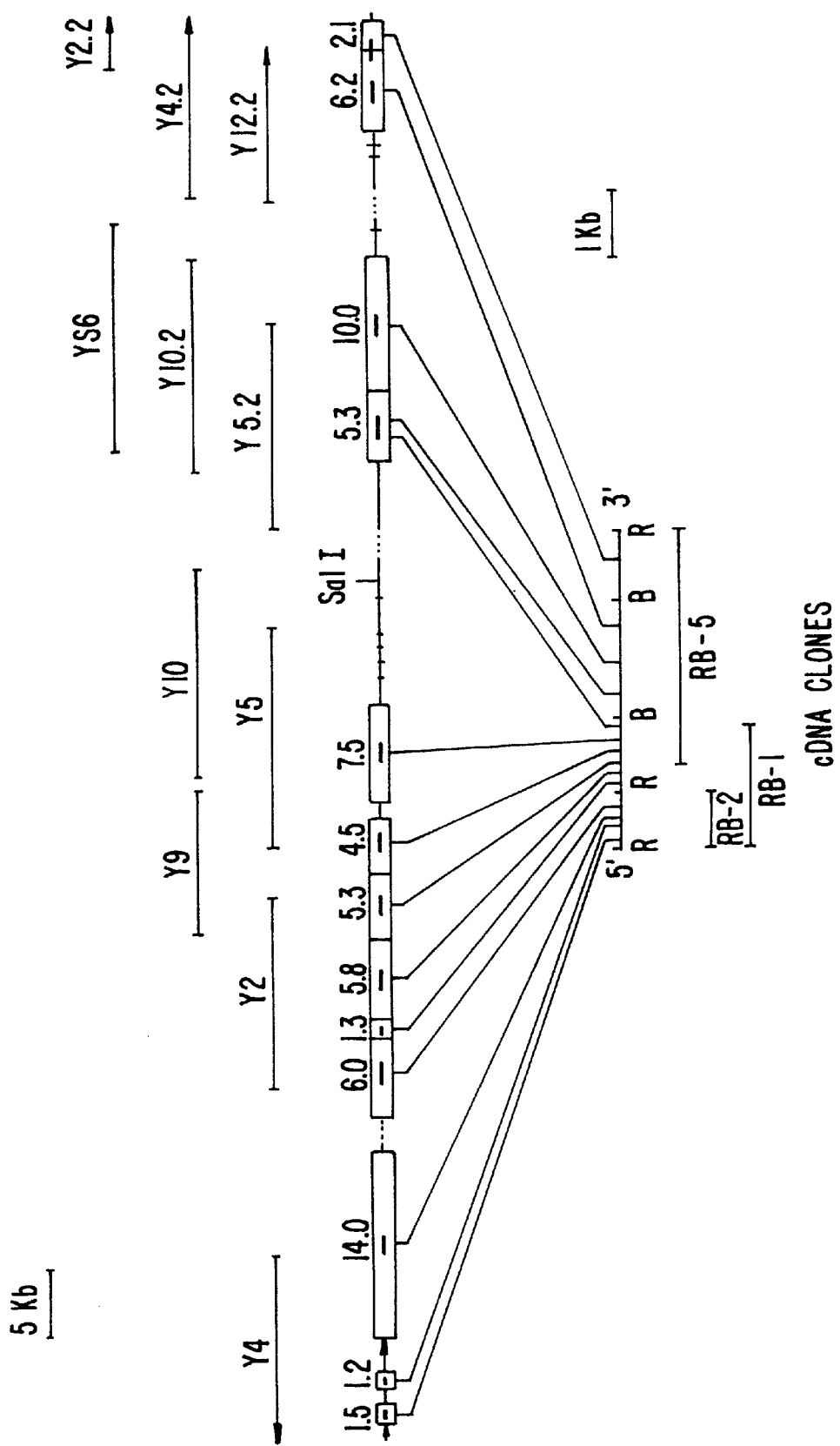
FIG. 4 is the drawing illustrating genomic DNA clones of the RB gene.

FIG. 4 is the drawing illustrating the genomic organization of the RB gene and physical relationship to its mRNA transcript. A simplified restriction map of RB cDNA is shown on the bottom, where R=Eco RI site and B=Bgl II site. Transcriptional orientation was determined. RB-1 and RB-5 cDNA clones were then used to screen an EMBL-3 genomic phage library constructed from retinoblastoma cell line Y79 as described in FIG. 1. About 20 relevant phage clones were isolated, of which the nonredundant ones are shown on the top. Characterization of these clones included Hind III restriction mapping by the cos method, and DNA blotting analysis with cDNA subfragments as probes to establish their physical relationship with genomic fragments. The genomic map, shown in the middle was constructed from this data and from data in FIG. 3. Hind III cleavage sites illustrated by vertical tics and Hind III fragments illustrated by boxes containing RB gene exons illustrated by solid bars are shown. A single Sal I site is present among all clones. Dotted lines represent intron regions. Additional exons may be present beyond the 5' end of the diagram.

Figure 5:
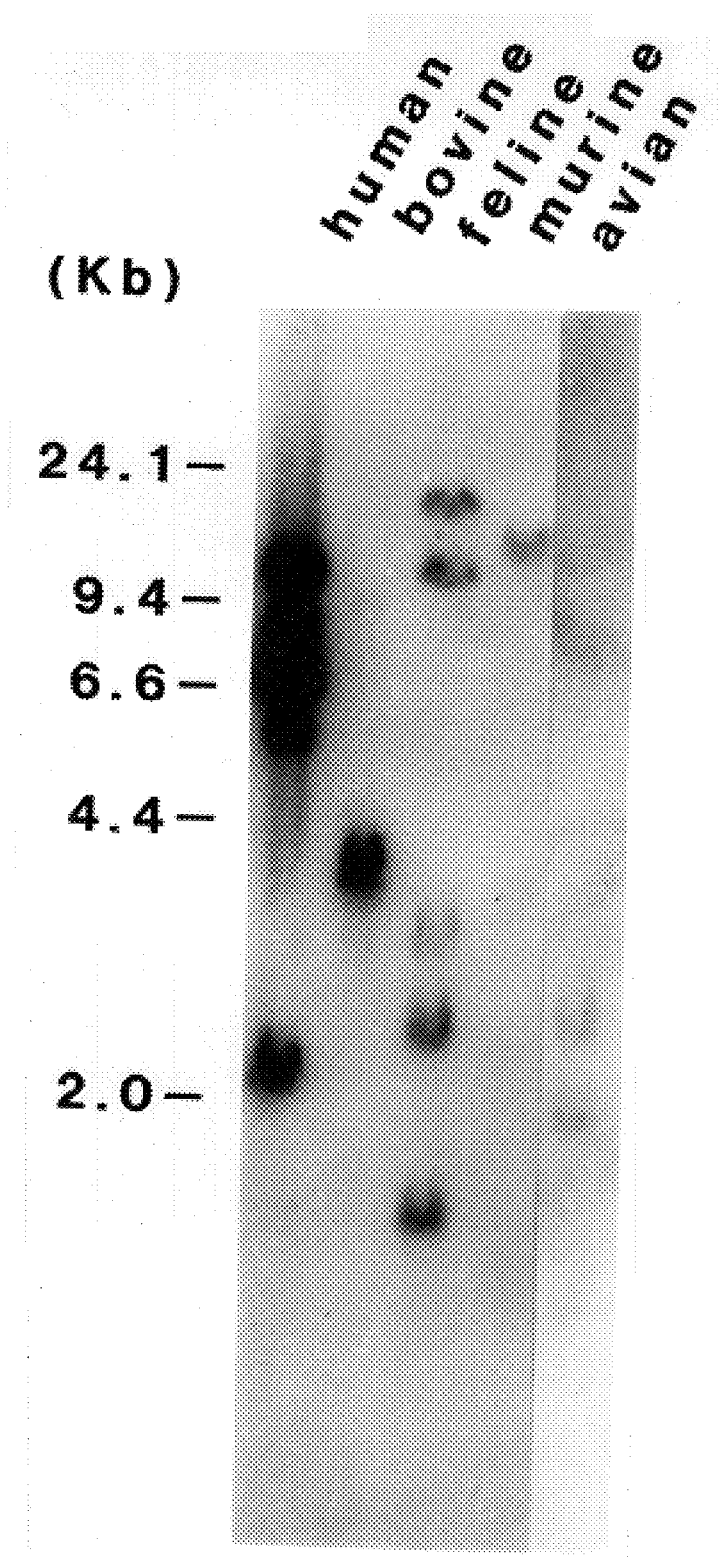
FIG. 5 is the chromatogram showing evolutionary conservation of the RB gene in vertebrates.

FIG. 5 is the chromatogram illustrating the evolutionary conservation of the RB gene in vertebrates. About 10 μg of DNA extracted from human placenta (lane 1), calf retina (lane 2), feline fibroblasts (lane 3), mouse NIH 3T3 fibroblasts (lane 4), and chicken embryo fibroblasts (lane 5) were digested with Hind III and separated by electrophoresis in 0.75% agarose gels. DNA fragments were then transferred to nitrocellulose and hybridized with $^{32}$P-labeled RB-5 cDNA as described for FIG. 3. At increased hybridization stringency (50% formamide), the signal for mouse and chicken became undetectable despite 7 days autoradiography.

Figure 6:
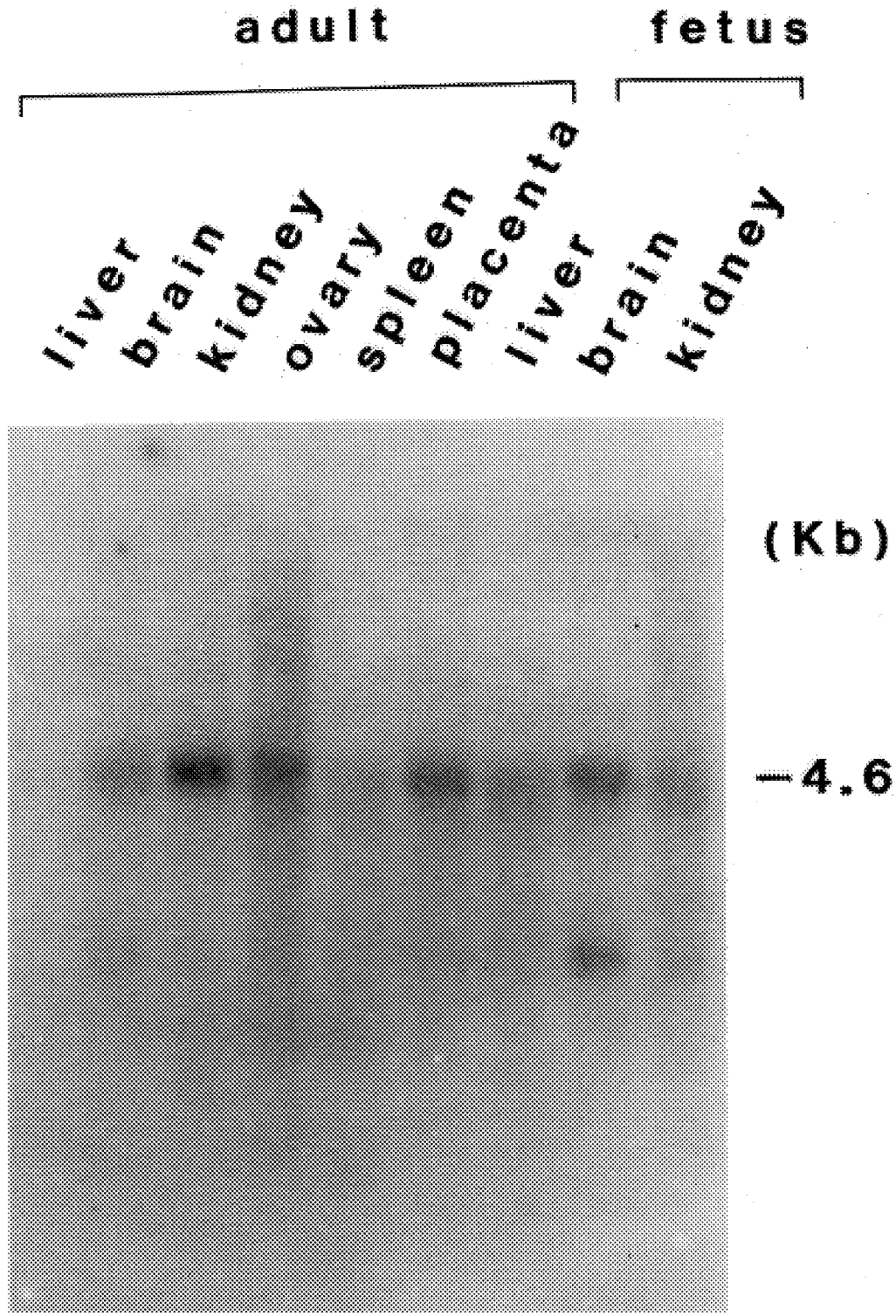
FIG. 6 is the chromatogram illustrating the tissue expression of the RB gene in rat.

FIG. 6 is the chromatogram illustrating the tissue expression of the RB gene in rat. Polyadenylated RNA was isolated from adult liver, brain, kidney, ovary, and spleen (lanes 1 to 5, respectively) ; from the placenta (lane 6); and from fetal (16-day gestation) rat tissues (liver, brain, and kidney in lanes 7 to 9, respectively). About 5 μg of mRNA was loaded into each lane of a 1% formaldehyde-agarose gel and analyzed as described for FIG. 2. The probe used in this experiment was a 32P-labeled RB-1. Similar results were obtained with RB-5 probe.

FIG. 7 is the nucleotide and predicted amino acid sequences of the RB cDNA. RB-1 cDNA (SEQ ID NOS. 4 AND 5) (1.6 kb) Bgl II-digested RB-5 cDNA (yielding RB710, RB1.8, and RB1.0) and Y79 cDNA were subcloned into M13 mp11, mp19, and mp10. Contiguous deletion mutants were constructed and sequenced to obtain about 95% of the complete sequence. Confirmation of unclear regions and closing of sequence gaps were accomplished by synthesizing new oligonucleotide primers or by subclonginq small fragments into new M13 phage. Sequences were entered directly into and analyzed on a microcomputer with a gel reader and DNA sequence software (International Biotechnologies Inc., New Haven, Conn.). Each of 4757 nucleotides was sequenced an average of five items. Eco RI linkers are noted at both ends of the sequence. A short poly(A) tail (broken underline) and the polyadenylation signal sequence (AATAA)(solid underline) are-present near the 3' end. The translated amino acid sequence is shown, numbered from the first methionine residue. Two paired potential metal binding domains (sequences of the form [H or C]-$X_{3-5}$ [H or C] separated by 27 to 31 residues) are shown in boxes. The boundaries of a proline-rich region are marked by arrows. Symbol-designates termination codon.

FIG. 8 is the hydropathy plot of the predicted amino acid sequence of the RB gene. The predicted sequence shown in FIG. 7 was analyzed to illustrate the regional predominance of hydrophilic or hydrophobic residues. Amino acid position numbers appear at the left.

FIG. 9 is the chromatogram of the RNA blot analysis of RB and c-fos genes in tumor cell lines and normal tissues. Polyadenylated RNA (5 ug) prepared from placenta (lane 1), retinoblastoma cell line Y79 (lane 2), and osteosarcoma cell lines G292, TE85, 143B, SAOS2, U2OS, nd MG63 (lanes 3–8 respectively) were separated by electrophoresis in a 1% formaldehyde-agarose gel and transferred to a nitrocellulose filter with 20×SSC. The filter was hybridized with $^{32}$P-labeled RB-5 DNA (top panel) in 50% formamide/6×SSC/ 5×Denhardt's solution/0.1% SDS/100 ug/ml denatured salmon sperm DNA/10 mM phosphate buffer (pH 7.0) at 42° C. for 24–48 hours. Washing followed in 2×SSC/0.1% SDS at room temperature for 15 minutes twice and in 0.2×SSC/ 0.1% SDS at 65° C. for 30 minutes. Autoradiography was done on Kodak XAR-5 film at −70° C. for 4 days with an intensifying screen. The filter was rehybridized with $^{32}$P-labeled EL-22 DNA (bottom panel) as described above, except that autoradiographic exposure was 3 days.

Figure 10:
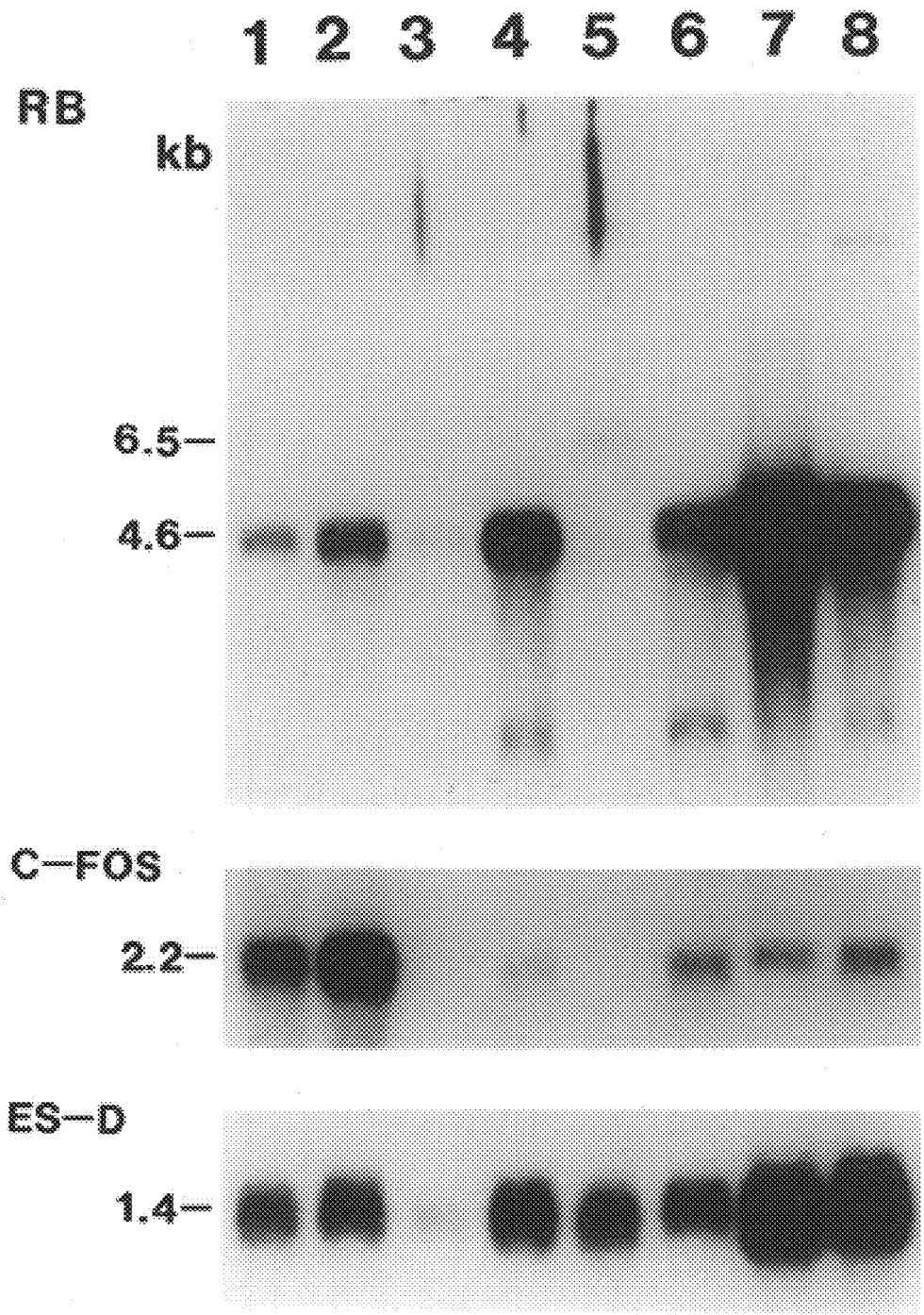
FIG. 10 is the chromatogram of RNA blot analysis of RB and c-fos genes in fresh-frozen tumors and normal tissue.

FIG. 10 is the chromatogram of the RNA blot analysis of RB and c-fos genes in fresh-frozen tumors and normal tissues. Polyadenylated RNA (5 ug) prepared from placenta (lane 1), fetal brain (lane 8), neuroblastoma cell line LAN-1 (lane 7), four fresh-frozen osteosarcoma samples (lanes 2, 3, 4, and 6) and one fresh-frozen synovial sarcom (lane 5) were analyzed as in FIG. 9 with probes RB-5 (top panel), fos (middle panel) and EL-22 (bottom panel).

FIG. 11A is the DNA blot analysis of genomic DNA fragments in osteosarcoma cell lines. About 10 ug of DNA extracted from normal human cells (lane 1), retinoblastoma cell line Y79 (lane 2), and osteosarcoma cell lines G292, TE85, 143B, SAOS2, U2OS, and MG63 (lanes 3–8 respectively) were digested with restriction enzyme Hind III, separated by electrophoresis in a 0.8% agarose gel, and transferred to a nitrocellulose filters with 10×SSC. The filter was hybridized with $^{32}$P-labeled RB-5 DNA in 40% formamide/6×SSC/5×Denhardt's solution/0.1% SDS/100 ug/ml denatured salmon sperm DNA/100 mM phosphate buffer (pH 7.0) at 42° C. for 48 hours. The filter was washed twice in 2×SSC/0.1% SDS at room temperature for 15 minutes and once in 0.2×SSC/0.1% SDS at 60° C. for 30 minutes. Filters were then autoradiographed as described for FIG. 10. SAOS2 (lane 6) lacks 10.0, 6.2 and 2.1 kb bands and has a new 12.0 kb band. MG63 (lane 8) shows an extra genomic band.

FIG. 11B is the drawing comparing the normal RB gene with a mutant allele of osteosarcoma cell lines SAOS2. The normal map was derived from more than 20 overlapping clones isolated from a genomic library screened with fragments of RB cDNA. Only the 3' portion of the gene is shown. Boxes represent exon-containing Hind III fragments detected by probe RB-5; additional Hind III cleavage sites are indicated by vertical tics. Dotted regions have not yet been mapped.

EXAMPLE 1

DNA Probes for Chromosomal Walking

Two chromosome 13 marker probes—esterase D EL22 clone and probe H3–8 were used as initial starting points for chromosomal walking. Both probes EL22 clone and H3–8 mapped to 13q14 region of chromosome 13, EL22 within 1500 kb from RB gene, H3–8 within 500 kb from esterase D gene.

EL22 cDNA Probe

Clone EL 22 cDNA was prepared according to procedure generally described in *Proc. Natl. Acad. Sci.*, 83:6337–6341 and 6790–6794 [1986].

Human esterase D (ESD) was purified to biochemical homogeneity from erythrocytes. The purification scheme included carboxy-metylcellulose, phenyl-Sepharose, chromatofocusing and hydroxylapeptide chromatography andresulted in 10,000-fold purification of the enzyme.

Purified human ESD protein was further treated with cyanogen bromide to obtain several cleaved peptides. The products were purified by reversed-phase HPLC (Brownlee RP 300).

After the eluted polypeptides were dried, their amino acid sequences were determined by solid-phase Edman degradation with HPLC analysis of the phenylthiohydration derivative as described in *Microcharacterization of Polypeptides: A Practical Manual*, Ed. J. E. Shively, Humana, Clifton, N.J. [1985]. The purified ESD protein was characterized by sequence analysis starting from the $NH_2$ terminus.

Each of the above obtained peptides sequences, or the portion thereof, was used for construction of synthetic oligonucleotide probes.

From the deduced amino acid sequences of peptides, the oligonucleotide mixtures corresponding to the possible coding sequences of each peptide were constructed. Mixed oligonucleotide probes were synthesized using phosphotriester chemistry on a synthesizer, located at the Department of Chemistry, University of California, San Diego. The oligonucleotide mixtures were purified by gel electrophoresis on 20% polyacrylamide/8 M urea gels and subsequently labeled at the 5' end with [γ$^{32}$P]ATP by using T4 polynucleotide kinase as described in *Molecular Cloning, A Laboratory Manual,* (Cold Spring Harbor Laboratory, Cold Springs Harbor, N.Y.).

23-mer probe was chemically synthesized having the following sequence: (SEQ ID NO.1)

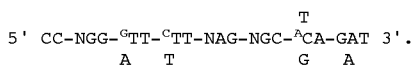

From the above nucleotide sequence the amino acid sequence was obtained as follows: (SEQ ID NO.2)

Ile-Lys-Ala-Leu-Lys-Asn-Pro-Gly.

This amino acid sequence then translated into the following nucleotide sequence: (SEQ ID NO.3)

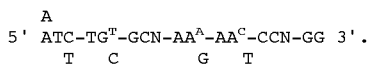

This sequence was used as 23-mer probe in subsequent screening for appropriate ESD clones.

The identical procedure was used for preparation of other oligomer probes used for RB gene sequencing.

Specific rabbit polyclonal anti-esterase D antibody was prepared and recognized both denatured or native human esterase D protein.

Purified esterase D and its specific antibody allowed cloning of the esterase D gene. Esterase D cDNA clone was isolated and identified based on three pieces of evidence:

(i) Esterase D cDNA encoded a protein immunologically related to esterase D protein;

(ii) The deduced amino acid sequences of the esterase D cDNA clone contained sequences identical to the three CNBr-cleaved peptides of the esterase D protein. (iii) Esterase D cDNA clone was mapped to chromosome 13q14 by Southern blotting using different deletion mutants.

Two λgt11 cDNA libraries constructed using human hepatoma mRNA according to procedure described in *DNA,* 3:437–447 (1984) and human placenta mRNA according to procedure in *J. Biol. Chem.,* 262:3112–3115 (1986), respectively, were plated on *E. coli* strain Y1090 and screened according to procedure described in *Proc. Natl. Acad. Sci.,* 80:1194–1198 [1983].

Two obtained inserts called EL22a and EL22b with identical 1.1 kilobases were induced to express β-galactosidase fusion protein.

In the recombinant lysogen of EL22a and EL22b, a fusion protein of 145 kDa was detected. The protein of β-galactosidase alone is 114 kDa and the remaining fragment of approximately ≈31 kDa was EL22.

The cloned EL22 was used as a probe in chromosomal walking and identification of RB gene.

H3–8 Probe

Probe H3–8 was derived form a phage library enriched for DNA sequences from chromosome 13 by using a fluorescence-activated chromosome sorter according to method described in *Cancer Genet. Cytogenet.,* 13:283–295 [1984]. Subsequently, it was used as the second probe for bidirectional chromosomal walking to identify RB gene.

EXAMPLE 2

Chromosomal Walking cDNA clone EL22 and H3–8 probes were used as initial starting points for bidirectional chromosomal walking to identify and isolate the retinoblastoma gene.

Both probes were used to screen plasmids Charon 30, Charon 4A, EMBL-3 or cosmid genomic libraries. These vectors and the method for constructing these libraries are described in *Molecular Cloning: A Laboratory Manual,* Cold Spring Harbor Laboratory, Cold Spring Harbor, N.Y. [1982]. DNA from human peripheral blood lymphocytes and from retinoblastoma cell line Y79, were used for screening *J. Natl. Cancer Inst.,* 53:347–352 [1974].

Esterase D gene is presumably located within 1500 kilobase range from RB gene and H3–8 probe is located within 500 kilobases from the esterase D gene.

In general, chromosomal walking was achieved by using esterase D complementary DNA clone EL22 to isolate its genomic clones. Distal DNA segments of these genomic clones were used in turn to isolate additional genomic clones. At 20 kilobases intervals in walking regions, unique sequences were identified, that were used as probes to isolate cDNA clones from fetal retina and placenta libraries. By alternately screening genomic and cDNA libraries, a bidirectional chromosome walking covering 120 kilobases was established. In this way, two cDNA clones, SD-1 an SD-2, were isolated by means of probes 5' to the esterase D gene. Chromosomal walking 3' to the esterase D encountered a 2C kilobases region containing highly repetitive sequences.

Bidirection chromosomal walking from the H3–8 probe was performed in the same manner as the one with EL22 clone described above. The walking extended over 30 kilobases and identified a unique DNA fragment H-1.2 which identified two overlapping cDNA clones. Both RB-1 the clone of 1.6 kilobases and the RB-2 clone 0.9 kilobases were identified from the human peripheral blood lymphocytes and from retinoblastoma cells cDNA libraries.

In greater detail, EL22 and H3–8 were used to screen genomic libraries from DNA of human peripheral blood lymphocytes or Y79 retinoblastoma cell lines. Unique sequence subfragments of genomic clones were used to screen λgt10 or λgt11 cDNA libraries obtained from fetal retinal or placental mRNA, yielding SD-1, SD-2 and RB-1.

DNA fragments were determined by the process of hybridization. The hybridization conditions were 6×SSC/5× Denhardt's solution/0.1% SDS at 65° C. Washing conditions were once in 2×SSC/0.1% SDS at room temperature and twice in 0.2×SSC/0.1% SDS at 65° C. for 30 minutes.

DNA fragments which contained repetitive sequences were determined by hybridizing with $^{32}$P-labeled total human genomic DNA as probe under the hybridization conditions in 40% formamide/6×SSC/5×Denhardt's solution/0.1% SDS/denatured salmon sperm DNA (100 μg ml)/100 mM phosphate buffer pH 7.0 at 42° for 24 hours.

Fragments which failed to hybridize were considered unique sequences and were used as the probes in screening. They were purified, labeled with $^{32}$p-(α)-dATP by nick translation or random oligonucleotide primer method according to *Anal. Biochem.,* 132: 6–13 [1983].

From the investigated fragments and from digestion sites obtained with several restriction enzymes, the consensus map was constructed.

The map is illustrated in FIG. 1.

EXAMPLE 3

The mRNA Expression of Genes in 13q14 region

Candidate RB gene obtained by chromosomal walking namely SD-1, SD-2 and RB-1 were used as probes in RNA blotting analysis to detect relevant mRNA transcripts.

Polyadenylated RNA was prepared and isolated from human fetal retinas obtained by dissection of about 25 first or second trimester fetal eyes, from portion of normal human placentas, from cultured cells of six retinoblastomas, three neuroblastoma, one medulloblastoma and one primary medulloblastoma.

The following Table 1 illustrates the expression of genes located in close proximity of RB gene and in its mapped region.

Esterase D gene transcripts were detectable in all control and tumor tissue samples.

SD-1 and SD-2's transcripts hybridizing to these clones were not detected in retina and placenta mRNA, although their expression was expected due to the fact that they were (SD-1 and SD-2 clones) obtained from placental and fetal retinal cDNA libraries. The SD-1 and SD-2 transcripts were also not detected in neuroblastoma. Therefore, neither of these genes seems promising as an RB gene candidate.

RB-1 clone transcript, on the other hand, was expressed in normal placental and fetal retinal tissue. It was present in neuroblastoma and medulloblastoma tissue in unaltered form. Four out of six retinoblastomas had shown expressed transcripts mRNA in altered size and two of the retinoblastomas showed no transcript mRNA at all. These findings provided necessary evidence that RB-1 cDNA is truly whole or a portion of the retinoblastoma gene.

TABLE 1

| | Probes | | | |
|---|---|---|---|---|
| Cells | Est | SD-1 | SD-2 | RB-1 |
| Placenta | + | −(+) | − | + |
| Fetal retina | + | − | −(+) | + |
| Retinoblastoma | | | | |
| 1 | + | − | − | +/alt |
| 2 | + | − | − | +/alt |
| 3 | + | − | − | − |
| 4 | + | − | −/alt | ±/alt |
| 5 | + | − | − | +/alt |
| 6 | + | − | − | +/alt |
| Neuroblastoma | | | | |
| 1 | + | − | − | + |
| 2 | + | − | − | + |
| 3 | + | − | − | + |
| Medulloblastoma | | | | |
| 1 | + | ND | ND | + |
| 2 | + | ND | ND | + |

Abbreviations are as follows:
Est = Esterase D
SD-1 = SD-1 clone
RB-1 = RB-1 clone
SD-2 = SD-2 clone
ND = not done
alt = altered mRNA size
+ = detectable mRNA expression
− = no detectable expression
(+) = expression expected

EXAMPLE 4

RNA Blot Analysis of RB Gene Transcripts

The same tissues as used in Example 3, namely human fetal retina, human placenta, six cultured retinoblastoma cell lines, three neuroblastoma cell lines, one medulloblastoma cell line and one medulloblastoma fresh tumor were used in RNA blot analysis.

The RNA (2–5 $\mu$g) from the above tissue samples were first polyadenylated and then separated by electrophoresis in 1% formaldehyde—agarose gels and transferred to nitrocellulose filters with 20×SSC. Filters were hybridized with $^{32}$-P-labeled RB-1 DNA in 50% formaldehyde/6×SSC/5× Denhardt's solution/0.1% SDS/denatured salmon sperm DNA (100 $\mu$g/ml) 10 mM phosphate buffer pH 7.0 at 42° C. for 24 hours. The samples were washed once with 2×SSC/0.1% SDS at room temperature for 20 minutes and twice in 0.1×SSC/0.1% SDS at 65° C. for 30 minutes. Autoradiography was done with Kodak XAR-5 film at −70° C. for 3 days with an intensifying screen.

Filters were then rehybridized with $^{32}$P-labeled EL-22 DNA as described above and exposed for 3 days.

The results are illustrated in FIG. 2. Esterase D transcripts were detected in all tumor and tissue samples. RB-1 hybridized with a 4.6 kilobases mRNA transcript in fetal retina and placenta. In three of five retinoblastoma samples, abnormal mRNA transcripts of approximately 40 kilobases were detected by RB-1. In two retinoblastoma, mRNA transcripts were not detected at all and in one sample there was a fault band of about 4.5 kilobases.

The experiments with samples missing the mRMA transcripts were repeated with overloading of the sample and by prolonged autoradiographic exposure. Even under these conditions, no mRNA was detectable.

Two other investigated tumors neuroblastoma and medulloblastoma displayed identical transcripts of 4.6 kilobases, equivalent to those of appearing in normal tissues.

The findings of mRNA transcripts in normal and nonretinoblastoma tumor tissues and altered or missing mRNA in retinoblastoma tissue indicate that RB-1 is a part of the putative RB gene.

A complete cDNA clone was sought by rescreening the two cDNA libraries with RB-1 as probe. Clone RB-5, with a 3.5-kb insert, was then isolated; it gave identical results as RB-1 in mRNA hybridization. Restriction enzyme analysis suggested that RB-5 and RB-1 overlapped in a 0.4-kb region, and together defined a DNA segment of about 4.6 kb, a size close to that of the normal mRNA transcript. For ease of analysis, the following probes were generated: RB-1 was cleaved by Eco RI into 0.9-kb (RBO.9) and 0.7-kb (RB0.7) fragments. RB-5 was cleaved by Bgl II into three fragments called RB710 (0.7 kb, Eco RI-Bgl II), RB1.8 (1.8 kb, Bgl II-Bgl II), and RB1.0 (1.0 kb, Bgl II-Eco RI).

EXAMPLE 5

DNA Blot Analysis of Genomic DNA Fragments

Normal human placental tissue and normal human fetal retinal tissue obtained by dissection of about 25 first or second trimester fetal eyes were used as controls. Cultured cell lines of six retinoblastomas, three neuroblastomas, one medulloblastoma, and one fresh medulloblastoma were used as experimental tissues.

All cells were grown in Dulbecco's modified Eagle's medium (GIBCO) supplemented with 10% fetal calf serum.

DNA was extracted from these cells using a method described in *Molecular Cloning: A Laboratory Manual,* (Cold Spring Harbor laboratory, Cold Spring Harbor, N.Y. [1982].

About 10 μg of extracted DNA from each sample was digested with restriction endonuclease enzyme Hind III (Haemophilus influenza Rd) and separated by electrophoresis in 0.75% agarose gel. The digested DNA fragments were then transferred onto a nitrocellulose filters with 10×SSC at 37° C., where 1×SSC equals 0.15 M NaCl/0.015 M sodium citrate.

Filters were hybridized with $^{32}$P-labeled RB-5 clone DNA or $^{32}$P-labeled RB 0.9 clone DNA in 40% formamide/6× SSC/5×Denhardt's solution/0.1% SDS/denatured salmon sperm DNA (100 μg/ml)/100 mM phosphate buffer pH 7.0 at 0.1% SDS at room temperature for 15 minutes and once in 0.2×SSC/0.1% SDS at 60° C. for 30 minutes.

DNA-quantitation was verified by washing filters at 95° C. to remove excess of free probes and then hybridizing using the same procedure as described above. Hybridization was achieved with a $^{32}$P-labeled human growth hormone gene fragment according to procedure described in *Nucleic Acid Res.,* 9:3719–3730 [1981].

The results are summarized in FIG. 3. Band intensities of DNA indicate that samples 5 and 6 (retinoblastoma) and 7 (control) have twice as much DNA as sample 4 (retinoblastoma) and half as much DNA as samples 1 and 2 (retinoblastomas). Sample 3 does not seem to have any DNA. These results show that retinoblastoma samples 1, 2, 5 and 6 have 2 copies of RB gene, retinoblastoma sample 4 has one copy and retinoblastoma sample 3 has none.

EXAMPLE 6
Nucleotide Sequence analysis of RB Gene

Isolated clones RB 1 and RB-5 were submitted to sequence analysis according to methods described in *Proc. Natl. Acad. Sci.,* 74:5463–5467 [1977] and *Plasmid,* 13:31–40 [1985].

Sequence analysis of clones RB-1, RB-5, and Y79 RB was performed by the dideoxyterminator method to yield the reconstructed complete cDNA sequence.

Different deletion templates were generated by the "cyclone" method described in *Plasmid,* 13:31–40 [1985]. RB-1 cDNA and BglII-digested RB-5 cDNA subclones RB710, BR1.8, and RB1.0 were subcloned into M13 mp11, mp19, and mp10. The subclones, using a single-stranded M13 DNA were generated as follows:

The oligomer, prepared in Example 1 was annealed to single-stranded M13 DNA. The DNA was cut at a restriction site within the annealed region with Hind III or EcoRI. The DNA insert was digested using the 3' and 5' exonuclease activity of T4 DNA polymerase. A short homopolymeric tail was added to the 3' end of the insert. DNA was ligated and used for transformation. Appropriate clones were picked, grown and sized on agarose gels and the template from the appropriate clones were prepared followed by sequencing.

The experimental conditions used in the above procedure are described in *Plasmid, (Ibid).*

Contiguous deletion mutants were constructed and sequenced according to method in *Proc. Natl. Acad. Sci.,* 74:5463–5467 [1977], and yielded greater than 95% of the sequence. The remaining gaps were sequenced by primer extension on both strands.

Confirmation of unclear regions and closing of sequence gaps were accomplished by synthesizing new oligomeric primers according to method of Example 1 or by subcloning small fragments into new M13 phage.

Sequences were entered directly into and analyzed on a microcomputer with a gel reader and DNA sequence software provided by International Biotechnologies, Inc., New Haven, Conn.

Each of 4757 obtained nucleotides were sequenced an average of five times.

The complete sequence contained 4757 nucleotides, with a short poly(A) tail and a polyadenylation signal sequence (AATAA) near the 3' end. An open reading frame was present from the 5' end to base 2688, with numerous additional in-frame stop codons further downstream. Translation from the first methionine codon yielded a hypothetical protein of 928 amino acids (110,000 daltons in size). A computer search of the National Biological Research Foundation protein sequence database detected no strong homology, with any more than 4000 published amino acid sequences. However, a number of nucleic acid-binding protein and viral proteins showed weak sequence homology, with a yeast DNA-directed RNA polymerase having the highest homology score.

The predicted protein sequence included ten potential glycosylation sites but a candidate transmembrane domain (at least 20 consecutive hydrophobic residues) was not found. The amino acid hydropathy plot (FIG. 8) showed a mildly hydrophobic region near the putative amino terminus and hydrophilic region at the carboxyl terminus. Two pairs of short amino acid sequences that were bracketed by cysteine and histidine residues in the manner of metal-binding domains found in nucleic acid-binding proteins were identified. A region of 54 amino acids from position 663 to 716 contains 14 praline residues (26%).

The complete nucleotide and amino acid sequence is shown in FIG. 7.

EXAMPLE 7
Expression of RB and C-FOS genes in Human Osteosarcoma

In order to delineate the roles of both RB and fos genes in the genesis of osteosarcoma, a panel of osteosarcoma call lines and tumors were surveyed for expression of these genes.

Polyadenylated RNA was prepared according to procedure in *Molecular Cloning: A Laboratory Manual,* Cold Spring Harbor Laboratory, Cold Spring Harbor, N.Y. RNA was extracted from six osteosarcoma cell lines as well as snap frozen (−70° C.) samples of four unfixed primary or metastatic osteosarcomas and one so-called synovial sarcoma, a soft-tissue tumor of unknown origin consisting mostly of typical fibrosarcomatous spindle cells.

RNA Blot Analysis

Polyadenylated RNA (5 μg) prepared form placenta retinoblastoma cell line Y79 and osteosarcoma cell lines G292, TE85, 143B, SAOS2, U2OS, were separated by electrophoresis in a 1% formaldehyde-agarose gel and transferred to a nitrocellulose filter with 20×SSC. The filter was hybridized with $^{32}$P-labeled RB-5 DNA in 50% formamide/6× SSC/5×Denhardt's solution/0.1% SDS/100 lg/ml denatured salmon sperm DNA/10 mM phosphate buffer(ph 7.0) at 42°

C. FOR 24–48 hours. Washing followed in 2×SSC/0.1% SDS at room temperature for 15 minutes twice and in 0.2×SSC/0.1% SDS at 65° C. for 30 minutes. Autoradiography was done on Kodak XAR-5 film at −70° C. for 4 days with an intensifying screen. The filter was rehybridized with $^{32}$P-labeled fos DNA and the 32P-labeled EL22 DNA as desribed above, in Example 1. Autoradiographic exposure was 3 days.

DNA Blot Analysis

About 10 μg of DNA extracted from normal human cells, retinoblastoma cell line Y79, and osteosarcoma cell lines G292, TE8S,143B, SAOS2, U2OS, and MG63 were digested with restriction enzyme Hind III, separated by electrophoresis in a 0.8% agarose gel, and transferred to a nitrocellulose filters with 10×SSC. The filter was hybridized with $^{32}$P-labeled RB-5 DNA in 40% formamide/6×SSC/5× Denhardt's solution/0.1% SDS/100 μg/ml denatured salmon sperm DNA/100 mM phosphate Buffer (pH 7.0) at 42° C. for 48 hours. The filter was washed twice in 2×SSC/0.1% SDS at RT for 15 minutes and once in 0.2×SSC/0.1% SDS at 60° C. for 30 minutes. Filters were then autoradiographed as described for FIG. 10.

The results are shown in FIG. 11. SAOS2 (lane 6) lacks 10.0, 6.2 and 2.1 kb bands and has a new 12.0 kb band. MG63 (lane 8) shows an extra genomic band, the origin of which is unknown.

Comparison of the normal RB gene with a mutant allele of osteosarcome SAOS2, was also made. The normal map was derived from more than 20 overlapping clones isolated from a genomic library screened with fragments of RB cDNA. Only the 3' portion of the gene is shown. Boxes represent exon-containing Hind III fragments detected by probe RB-5; additional Hind III cleavage sites are indicated (vertical tics). Dotted regions are not yet mapped.

Hybridization of probe EL22, which detects the ubiquitously expressed marker enzyme esterase D, was used as a control for mRNA quality. As expected, RB gene transcripts of normal length (4.6 kb) were detected in a neuroblastoma cell line (LAN-1) and in fetal brain and placenta, while a shortened mRNA was seen in retinoblastoma cell line Y79. Of six osteosarcoma cell lines, one (SAOS2) showed a shortened mRNA transcript of 3.7 kb. Based on findings i retinoblastomas, this change presumably indicates loss of RB gene function. The remaining five cell lines had transcripts of normal length, though that of one, U20s, was present in an extremely low quantity. Samples taken directly from four osteosarcoma tumors failed to show such mRNA alteration. Unexpectedly, the single fibrosarcoma-like tumor tested demonstrated an mRNA transcript of increased size (6.5 kb) in addition to the normal 4.6 kb transcript. The normal transcript may result from non-malignant cells that are necessarily intermixed in a solid tumor; or may be due to transcription from two different alleles in tumor cells. Both cell line and tumor RNA blots were washed and rehybridized with probes for c-fos. Cognate transcripts were detected in fetal brain and placenta, consonant with previous observations, as well as in neuroblastoma cell line LAN-1. Osteosarcoma tumor samples expressed variable amounts of fos mRNA, but in contrast it was undetectable in all osteosarcoma cell lines. It was also not detected in the synovial sarcoma, which served to further distinguish this sample from the other fresh-frozen tumors.

Genomic DNA was extracted from the same panel of cell lines and tumor samples as above and analyzed with RB gene probes. All but one sample showed a pattern of hybridization indistinguishable from normal human DNA while that of SAOS2 lacked three normal exon-containing Hind III fragments and had one additional novel fragment. Further analysis with subfragments of RB c DNA as probes indicated a homozygous partial DNA deletion in this case which, based on the RB genomic map, begins in the 10.0 kb Hind III band and extends beyond the 2.1 kb band at the 3' end. This is the first case in which deletion has been shown as the probable explanation for a shortened mRNA transcript. Despite its abnormal RB expression, the synovial sarcoma had a grossly normal RB gene, as has been seen in several retinoblastomas. Results of RNA blotting analysis are shown in FIGS. 9, 10 and 11 summarized in Table 1.

TABLE 2

|  | Probes | | |
| --- | --- | --- | --- |
|  | RB gene | c-fos | Es-D |
| Osteosarcoma Cell lines | | | |
| G292 | + | − | + |
| TE85 | + | − | + |
| 143B | + | − | + |
| SAOS2 | +/alt | − | + |
| U2OS | ± | − | + |
| MG636 | + | − | + |
| Tumors | | | |
| 1 | + | + | + |
| 2 | + | ± | + |
| 3 | + | + | + |
| 4 | + | + | + |
| Synovial sarcoma | | | |
| 1 | +/alt | − | + |
| Neuroblastoma | | | |
| LAN-1 | + | + | + |
| Retinoblastoma | | | |
| Y79 | +/alt | − | + |
| Normal tissue | | | |
| Placenta | + | + | + |
| Fetal brain | + | + | + |

Table 1. mRNA expression of genes is osteosarcoma, other tumors and normal tissues.

Abbreviations are as follows:

RB = retinoblastoma;

Es-d = esterase D;

+ = detectable mRNA expression;

− = no detectable expression;

± = weak expression;

alt = altered mRNA size.

What is claimed is:

1. A method of detecting a mutated retinoblastoma ("RB") nucleic acid in mammals, the method comprising the steps of:

(i) hybridizing an isolated full-length, wild-type RB cDNA probe to a cell sample; and (ii) detecting a mutated RB nucleic acid.

2. The method of claim 1, wherein the cell sample is human.

3. A method of detecting a mutated retinoblastoma ("RB") gene in a mammal, the method comprising the steps of:

(i) isolating RNA from a cell sample;

(ii) hybridizing the RNA with an isolated full-length, wild-type RB cDNA probe; and (iii) detecting the presence of an abnormal RB RNA, the presence of a normal RB RNA or absence of an RB RNA, wherein the presence of an abnormal RB RNA or the absence of an RB RNA indicates a mutated RB gene.

4. The method of claim 3, wherein the mammal is a human.

* * * * *

UNITED STATES PATENT AND TRADEMARK OFFICE
CERTIFICATE OF CORRECTION

PATENT NO.    : 5,998,134
DATED         : December 7, 1999
INVENTOR(S)   : Wen-Hwa Lee and Eva Y-H. P. Lee Page 1 of 1

It is certified that error appears in the above-identified patent and that said Letters Patent is hereby corrected as shown below:

Column 37,
Line 20, -- , wherein the full-length, wild-type RB cDNA probe has the nucleotide sequence depicted in Figure 7 -- should be inserted after "sample" and before "; and."
Line 17, -- , wherein the full-length, wild-type RB cDNA probe has the nucleotide sequence depicted in Figure 7 -- should be inserted after "probe" and before "; and."

Signed and Sealed this

Seventh Day of January, 2003

JAMES E. ROGAN
*Director of the United States Patent and Trademark Office*

Adverse Decisions in Interference

Patent No. 5,998,134, Wen-Hwa Lee, and Eva Y-H.P. Lee, RETINOBLASTOMA GENE-CANCER SUPPRESSOR AND REGULATOR, Interference No. 105,182, final judgment adverse to the patentees rendered December 7, 2005, as to claims 1-4.

*(Official Gazette March 20, 2007)*